（12） United States Patent
Bekele et al.

US009173824B2

(10) Patent No.: US 9,173,824 B2
(45) Date of Patent: Nov. 3, 2015

(54) MASCARA AND APPLICATOR

(75) Inventors: Haiminot Bekele, Baltimore, MD (US); Gwen Trinidad Acierto Cabanez, Owings Mills, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 563 days.

(21) Appl. No.: 13/471,603

(22) Filed: May 15, 2012

(65) Prior Publication Data
US 2012/0315076 A1 Dec. 13, 2012

Related U.S. Application Data

(60) Provisional application No. 61/487,149, filed on May 17, 2011.

(51) Int. Cl.
*A61Q 1/10* (2006.01)
*A61K 8/37* (2006.01)
*A61K 8/92* (2006.01)
*A45D 40/26* (2006.01)
*A46B 3/18* (2006.01)

(52) U.S. Cl.
CPC ................. *A61K 8/375* (2013.01); *A61K 8/922* (2013.01); *A61Q 1/10* (2013.01); *A45D 40/265* (2013.01); *A46B 3/18* (2013.01); *A61K 2800/87* (2013.01); *A61K 2800/88* (2013.01)

(58) Field of Classification Search
None
See application file for complete search history.

(56) References Cited

U.S. PATENT DOCUMENTS

| | | |
|---|---|---|
| 2,458,063 A | 1/1949 | Duhlberg |
| 2,831,854 A | 4/1958 | Tucker |
| 2,900,306 A | 8/1959 | Slater |
| 3,255,082 A | 6/1966 | Barton |
| 3,677,271 A | 7/1972 | Luciano |
| 3,690,777 A | 9/1972 | Costa |
| 3,739,789 A | 6/1973 | Cataneo |
| 3,802,841 A | 4/1974 | Robin |
| 3,963,699 A | 6/1976 | Rizzi et al. |
| 4,005,195 A | 1/1977 | Jandacek |
| 4,005,196 A | 1/1977 | Jandacek et al. |
| 4,126,679 A | 11/1978 | Davy et al. |
| 4,137,306 A | 1/1979 | Rubino et al. |
| 4,151,272 A | 4/1979 | Geary et al. |
| 4,154,816 A | 5/1979 | Roehl et al. |
| D252,911 S | 9/1979 | Levy |
| 4,202,879 A | 5/1980 | Shelton |
| 4,226,889 A | 10/1980 | Yuhas |
| 4,228,277 A | 10/1980 | Landoll |
| 4,229,432 A | 10/1980 | Geria |
| 4,280,994 A | 7/1981 | Turney |
| 4,322,400 A | 3/1982 | Yuhas |
| 4,336,246 A | 6/1982 | Leon-Pekarek |
| 4,346,079 A | 8/1982 | Roehl |
| D267,822 S | 2/1983 | Katz |
| 4,383,988 A | 5/1983 | Teng et al. |
| D277,324 S | 1/1985 | Davey |
| 4,517,360 A | 5/1985 | Volpenhein |
| 4,518,772 A | 5/1985 | Volpenhein |
| 4,725,432 A | 2/1988 | May |
| 4,759,924 A | 7/1988 | Luebbe et al. |
| 4,797,300 A | 1/1989 | Jandacek et al. |
| 4,816,261 A | 3/1989 | Luebbe et al. |
| 4,886,080 A | 12/1989 | Cole |
| 4,932,802 A | 6/1990 | Cantone |
| 4,980,155 A | 12/1990 | Shah et al. |
| 4,993,858 A | 2/1991 | Mock |
| 5,017,398 A | 5/1991 | Jandacek et al. |
| 5,019,375 A | 5/1991 | Tanner et al. |
| 5,040,914 A | 8/1991 | Fitjer |
| 5,056,179 A | 10/1991 | Capponi |
| 5,097,853 A | 3/1992 | Nehashi |
| 5,104,646 A | 4/1992 | Bolich, Jr. et al. |
| 5,165,917 A | 11/1992 | Zabotto |
| 5,193,918 A | 3/1993 | Lohrmann et al. |
| 5,217,641 A | 6/1993 | Herstein |
| 5,306,514 A | 4/1994 | Letton et al. |
| 5,306,515 A | 4/1994 | Letton et al. |
| 5,306,516 A | 4/1994 | Letton et al. |
| RE34,617 E | 5/1994 | Jandacek et al. |
| D348,123 S | 6/1994 | Wu |
| 5,376,231 A | 12/1994 | Matsumoto et al. |
| 5,389,363 A | 2/1995 | Snyder |
| D360,486 S | 7/1995 | Schultz |
| 5,490,529 A | 2/1996 | Fitjer |

(Continued)

FOREIGN PATENT DOCUMENTS

| | | |
|---|---|---|
| CN | 102360418 A | 2/2012 |
| DE | 3923731 A1 | 1/1991 |

(Continued)

OTHER PUBLICATIONS

Avon, Avon Colour, In a Blink Eye Shadow and Liner, date published Mar. 2007; www.gnpd.com, 2 pages.
Avon, Avon, Blueberry Cool/Black Lush Lips and Long Lashes, date published Mar. 2006; www.gnpd.com, 2 pages.
Avon, Avon, Dual Ended Eye-Liner, date published Oct. 2007; www.gnpd.com, 2 pages.
Avon, Avon, Shimmer Shadow and Liner, date published Jun. 2007; www.gnpd.com, 2 pages.
Avon, MistakeProof Mascara, date published Oct. 2008; www.gnpd.com , 4pages.
Bare Escentuals, bareMinerals Tutorials, Lesson 1: Get Cheeky, date published Feb. 2008; www.gnpd.com, 1 page.
Bare Escentuals, bareMinerals, Get Started: Eyes, Cheeks, Lips Set, date published Mar. 2008; www.gnpd.com, 1 page.

(Continued)

*Primary Examiner* — Jyothsna Venkat
(74) *Attorney, Agent, or Firm* — Betty J. Zea

(57) ABSTRACT

A semi-permanent mascara product that includes a supply of a semi-permanent mascara composition disposed in a container and a twisted-wire brush for applying the mascara to the eyelashes of a user. The combination of the semi-permanent mascara and twisted-wire brush provides improved eyelash separation and reduced clumping versus the same mascara composition and an unsuitable molded plastic brush.

1 Claim, 16 Drawing Sheets

(56) References Cited

U.S. PATENT DOCUMENTS

| | | | |
|---|---|---|---|
| 5,509,742 A | 4/1996 | Balzarini |
| D370,088 S | 5/1996 | Burns |
| 5,794,632 A | 8/1998 | Gueret |
| 5,832,942 A | 11/1998 | Gutberlet |
| 5,866,434 A | 2/1999 | Massey et al. |
| D419,266 S | 1/2000 | Gobe |
| D422,748 S | 4/2000 | Lang |
| 6,071,503 A | 6/2000 | Drechsler et al. |
| 6,074,654 A | 6/2000 | Drechsler et al. |
| 6,080,687 A | 6/2000 | Ishwarlal |
| 6,139,823 A | 10/2000 | Drechsler et al. |
| 6,200,045 B1 | 3/2001 | Hahn et al. |
| 6,203,814 B1 | 3/2001 | Fisher et al. |
| 6,241,408 B1 | 6/2001 | Lang |
| 6,267,951 B1 | 7/2001 | Shah et al. |
| 6,303,105 B1 | 10/2001 | Shah et al. |
| D450,888 S | 11/2001 | Breidenbach et al. |
| 6,340,466 B1 | 1/2002 | Drechsler et al. |
| D453,588 S | 2/2002 | Breidenbach et al. |
| D453,589 S | 2/2002 | Breidenbach et al. |
| 6,450,179 B2 | 9/2002 | Bengis |
| 6,464,418 B1 | 10/2002 | Visser |
| 6,488,427 B1 | 12/2002 | Breidenbach et al. |
| 6,491,902 B2 | 12/2002 | Shefer et al. |
| 6,500,446 B1 | 12/2002 | Derrieu et al. |
| 6,502,584 B1 * | 1/2003 | Fordham ..................... 132/218 |
| D474,341 S | 5/2003 | Cantone et al. |
| 6,612,764 B2 | 9/2003 | Dumler |
| 6,637,963 B2 | 10/2003 | Huang |
| D482,284 S | 11/2003 | Cantone et al. |
| 6,682,242 B1 | 1/2004 | Montoli |
| 6,702,494 B2 | 3/2004 | Dumler |
| D491,810 S | 6/2004 | Kostow |
| D491,811 S | 6/2004 | Kostow |
| D497,455 S | 10/2004 | Lee |
| 6,811,770 B2 | 11/2004 | Ferrari et al. |
| 6,827,516 B2 | 12/2004 | Gutberlet |
| 6,896,433 B1 | 5/2005 | Zhang |
| 6,979,440 B2 | 12/2005 | Shefer et al. |
| 6,985,879 B2 | 1/2006 | Walker et al. |
| 7,077,591 B2 | 7/2006 | Gueret |
| D530,857 S | 10/2006 | Black |
| 7,168,875 B1 | 1/2007 | Zhang |
| 7,175,359 B2 | 2/2007 | Zhang |
| 7,186,274 B2 | 3/2007 | Vic et al. |
| D542,978 S | 5/2007 | Bortolotti |
| 7,210,870 B2 | 5/2007 | Breidenbach et al. |
| 7,226,227 B2 | 6/2007 | Gueret |
| 7,241,835 B2 | 7/2007 | O'Brien et al. |
| 7,276,088 B2 | 10/2007 | Huang et al. |
| D561,390 S | 2/2008 | Sugawara |
| D566,335 S | 4/2008 | Althoff et al. |
| D566,337 S | 4/2008 | Althoff et al. |
| D574,154 S | 8/2008 | Dumler et al. |
| D574,155 S | 8/2008 | Dumler et al. |
| D578,770 S | 10/2008 | Berhault |
| D579,208 S | 10/2008 | Berhault |
| 7,438,953 B2 | 10/2008 | Kotov et al. |
| D581,169 S | 11/2008 | Berhault |
| D583,506 S | 12/2008 | Justice |
| D585,600 S | 1/2009 | Althoff et al. |
| 7,473,045 B2 | 1/2009 | Dumler |
| D592,858 S | 5/2009 | Berhault |
| D593,330 S | 6/2009 | Berhault |
| D593,331 S | 6/2009 | Berhault |
| D598,657 S | 8/2009 | Berhault |
| D600,921 S | 9/2009 | Berhault |
| D600,922 S | 9/2009 | Berhault |
| D600,923 S | 9/2009 | Berhault |
| D615,419 S | 5/2010 | Owen |
| 7,780,875 B2 | 8/2010 | Asgari |
| 7,842,285 B2 | 11/2010 | Lu et al. |
| 7,856,806 B1 | 12/2010 | Chasman et al. |
| D634,478 S | 3/2011 | Kolas et al. |
| 7,993,661 B2 | 8/2011 | Arnaud et al. |
| 8,096,306 B2 | 1/2012 | Malvar et al. |
| D654,626 S | 2/2012 | Kolas et al. |
| 8,323,628 B2 | 12/2012 | Atis |
| 8,329,147 B2 | 12/2012 | Ansmann et al. |
| 8,335,560 B2 | 12/2012 | Dumler et al. |
| 2001/0051168 A1 | 12/2001 | Ramin et al. |
| 2002/0071707 A1 | 6/2002 | Breidenbach |
| 2002/0076390 A1 | 6/2002 | Kantner et al. |
| 2002/0083954 A1 | 7/2002 | Gavney |
| 2002/0185148 A1 | 12/2002 | Bengis |
| 2002/0190336 A1 | 12/2002 | Shimizu et al. |
| 2003/0041870 A1 | 3/2003 | Su |
| 2003/0086741 A1 | 5/2003 | Kim |
| 2003/0095935 A1 | 5/2003 | Chaiyawat et al. |
| 2003/0143181 A1 | 7/2003 | Hensen et al. |
| 2004/0105828 A1 | 6/2004 | Chaiyawat et al. |
| 2004/0115232 A1 | 6/2004 | Giroud et al. |
| 2004/0126303 A1 | 7/2004 | Hwang |
| 2004/0190974 A1 | 9/2004 | Cantone et al. |
| 2004/0228890 A1 | 11/2004 | Blin et al. |
| 2004/0234564 A1 | 11/2004 | Blin et al. |
| 2005/0095213 A1 | 5/2005 | Blin et al. |
| 2005/0176598 A1 | 8/2005 | Bergquist et al. |
| 2005/0186167 A1 | 8/2005 | Ueda et al. |
| 2005/0276779 A1 | 12/2005 | Blin |
| 2006/0029560 A1 | 2/2006 | Blin |
| 2006/0067783 A1 | 3/2006 | Tsaur |
| 2006/0127339 A1 | 6/2006 | Bavouzet et al. |
| 2006/0134035 A1 | 6/2006 | Zheng et al. |
| 2006/0189554 A1 | 8/2006 | Mumper et al. |
| 2006/0260633 A1 | 11/2006 | Wyatt et al. |
| 2006/0275232 A1 | 12/2006 | Chevalier |
| 2007/0020205 A1 | 1/2007 | Blin et al. |
| 2007/0041920 A1 | 2/2007 | Blin et al. |
| 2007/0048238 A1 | 3/2007 | Sandewicz et al. |
| 2007/0140991 A1 | 6/2007 | Maitra et al. |
| 2007/0274941 A9 | 11/2007 | Blin |
| 2007/0286824 A1 | 12/2007 | Rabe et al. |
| 2008/0000491 A1 | 1/2008 | Bodelin |
| 2008/0014232 A1 | 1/2008 | Arnaud et al. |
| 2008/0056807 A1 | 3/2008 | Vintimiglia |
| 2008/0107615 A1 | 5/2008 | Keene et al. |
| 2008/0115798 A1 | 5/2008 | Rainey et al. |
| 2008/0124350 A1 | 5/2008 | Mumper et al. |
| 2008/0171009 A1 | 7/2008 | Auguste et al. |
| 2008/0226575 A1 | 9/2008 | Hanna |
| 2008/0311063 A1 | 12/2008 | Shah et al. |
| 2009/0010868 A1 | 1/2009 | Ilekti et al. |
| 2009/0098170 A1 | 4/2009 | D'Acchioli et al. |
| 2009/0142282 A1 | 6/2009 | Kendall et al. |
| 2009/0193692 A1 | 8/2009 | Lipczynski |
| 2009/0263658 A1 | 10/2009 | Alberius et al. |
| 2009/0317350 A1 | 12/2009 | Lu et al. |
| 2010/0003205 A1 | 1/2010 | Elliott et al. |
| 2010/0003293 A1 | 1/2010 | Elliott et al. |
| 2010/0028612 A1 | 2/2010 | Gruber et al. |
| 2010/0068163 A1 | 3/2010 | Lu |
| 2010/0074928 A1 | 3/2010 | Elliott et al. |
| 2010/0152135 A1 | 6/2010 | Blin |
| 2010/0179105 A1 | 7/2010 | Blin et al. |
| 2010/0285079 A1 * | 11/2010 | Imai et al. ..................... 424/401 |
| 2011/0094533 A1 | 4/2011 | Dempsey et al. |
| 2011/0094914 A1 | 4/2011 | Dempsey et al. |
| 2011/0117040 A1 | 5/2011 | Dempsey et al. |
| 2011/0117043 A1 | 5/2011 | Dempsey et al. |
| 2011/0268490 A1 | 11/2011 | Acierto et al. |
| 2012/0114585 A1 | 5/2012 | Dempsey et al. |
| 2012/0269753 A1 | 10/2012 | Rabe et al. |
| 2012/0298128 A1 | 11/2012 | Hodgetts et al. |
| 2012/0315076 A1 | 12/2012 | Bekele et al. |
| 2013/0012594 A1 | 1/2013 | Hirasawa et al. |
| 2013/0056016 A1 | 3/2013 | Guay et al. |
| 2013/0056019 A1 | 3/2013 | Wilson et al. |
| 2013/0056020 A1 | 3/2013 | Wilson et al. |

FOREIGN PATENT DOCUMENTS

| | | |
|---|---|---|
| EM | 000345483.003 | 7/2005 |
| EM | 000386388.0001 | 11/2005 |

(56) References Cited

FOREIGN PATENT DOCUMENTS

| | | |
|---|---|---|
| EM | 000386388.0002 | 11/2005 |
| EM | 000386388.0020 | 11/2005 |
| EM | 000386388.0028 | 11/2005 |
| EM | 000386388.0030 | 11/2005 |
| EM | 000386388.0031 | 11/2005 |
| EM | 000386388.0034 | 11/2005 |
| EM | 000500418.001 | 5/2006 |
| EM | 000540869.0021 | 7/2006 |
| EM | 000540869.0024 | 7/2006 |
| EM | 000603808.002 | 11/2006 |
| EM | 000623202.0002 | 12/2006 |
| EM | 000623202.0004 | 12/2006 |
| EM | 000623202.0009 | 12/2006 |
| EM | 000623202.0010 | 12/2006 |
| EM | 000623202.0011 | 12/2006 |
| EM | 000623202.0012 | 12/2006 |
| EM | 000623202.0013 | 12/2006 |
| EM | 000614706.001 | 1/2007 |
| EM | 000654272.0003 | 4/2007 |
| EM | 000654272.0004 | 4/2007 |
| EM | 000654272.0005 | 4/2007 |
| EM | 000688007.0002 | 4/2007 |
| EM | 000688007.0003 | 4/2007 |
| EM | 000871017.0001 | 2/2008 |
| EM | 000871017.0007 | 2/2008 |
| EM | 000871017.0008 | 2/2008 |
| EM | 000871017.0009 | 2/2008 |
| EM | 000871017.0010 | 2/2008 |
| EM | 000871017.0014 | 2/2008 |
| EM | 000871017.0015 | 2/2008 |
| EM | 000871017.0016 | 2/2008 |
| EM | 000871017.0024 | 2/2008 |
| EM | 000871017.0025 | 2/2008 |
| EM | 000871017.0026 | 2/2008 |
| EM | 000871017.0027 | 2/2008 |
| EM | 000871017.0028 | 2/2008 |
| EM | 000871017.0029 | 2/2008 |
| EM | 000871017.0030 | 2/2008 |
| EM | 000871017.0031 | 2/2008 |
| EM | 000871017.0032 | 2/2008 |
| EM | 000871017.0033 | 2/2008 |
| EM | 000871017.0037 | 2/2008 |
| EM | 000871017.0038 | 2/2008 |
| EM | 000871017.0039 | 2/2008 |
| EM | 000871017.0040 | 2/2008 |
| EM | 000871017.0043 | 2/2008 |
| EM | 000871017.0044 | 2/2008 |
| EM | 000871017.0054 | 2/2008 |
| EM | 000871017.0055 | 2/2008 |
| EM | 000871017.0056 | 2/2008 |
| EM | 000871017.0057 | 2/2008 |
| EM | 000871017.0058 | 2/2008 |
| EM | 000871017.0059 | 2/2008 |
| EM | 000871017.0060 | 2/2008 |
| EM | 000871017.0061 | 2/2008 |
| EP | 549494 | 6/1993 |
| FR | 000975286.0001 | 12/1997 |
| FR | 2919477 A1 | 2/2009 |
| GB | 2124081 A | 2/1984 |
| GB | 2293545 A | 4/1996 |
| JP | 03173811 | 7/1991 |
| JP | 2004188189 A | 7/2004 |
| JP | 2004238363 | 8/2004 |
| JP | 2004339212 A | 12/2004 |
| JP | 2006174936 A | 7/2006 |
| JP | 2006282585 | 10/2006 |
| JP | 2009114099 | 5/2009 |
| JP | 2009137841 | 6/2009 |
| WO | 000011033.003 | 7/1988 |
| WO | 000014434.0010 | 10/1989 |
| WO | 000014434.0011 | 10/1989 |
| WO | 000014434.0025 | 10/1989 |
| WO | 96/20698 | 7/1996 |
| WO | 000042185.0001 | 2/1998 |
| WO | 000042185.0002 | 2/1998 |
| WO | 000042185.0003 | 2/1998 |
| WO | 000042185.0004 | 2/1998 |
| WO | 00/47177 | 8/2000 |
| WO | 000054973.0006 | 3/2001 |
| WO | 01/45652 | 6/2001 |
| WO | 2004073662 A1 | 9/2004 |
| WO | 2006/058795 | 6/2006 |
| WO | 2006/078541 | 7/2006 |
| WO | 2008/074870 A2 | 6/2008 |
| WO | 2008089926 A | 7/2008 |
| WO | WO 2009/143004 | * 11/2009 |
| WO | 2012/011043 A1 | 1/2012 |

OTHER PUBLICATIONS

Bobbi Brown Copper Diamond, Everything/Lash Glamour Mascara Duo, date published Nov. 2008; www.gnpd.com, 3 pages.
Bobbi Brown, Bobbi Brown Christmas 2008, Night Sky Long-Wear Eye Palette, date published Dec. 2008; www.gnpd.com, 3 pages.
Bobbi Brown, Honey Glaze Long-Wear Eye Palette, date published Apr. 2009; www.gnpd.com, 3 pages.
Bobbi Brown, Lip and Eye Basics Palette, date published Sep. 2006; www.gnpd.com, 2 pages.
Bobbi Brown, Shimmering Nudes Collection, Shimmering Nudes Palette, date published Oct. 2008; www.gnpd.com, 3 pages.
Caboodles Color Tips, Mascara Extension, date published Dec. 2005; www.gnpd.com, 2 pages.
Cosmetobelleza Natural IM, Double Effect Mascara, date published: Jul. 2009; www.gnpd.com, 2 pages.
Creative Brands, Australis, Eyeshadow, date published Aug. 2007; www.gnpd.com, 2 pages.
Del Laboratories, Sally Hansen Healing Beauty, Thicken-Up Plumper + Mascara, date published Oct. 2003; www.gnpd.com, 2 pages.
Gurwitch Products, Laura Mercier, Limited-Edition Eye Book, date published Dec. 2008; www.gnpd.com, 2 pages.
Gurwitch Products, Laura Mercier, Beauty Library Set, date published Dec. 2006; www.gnpd.com, 3 pages.
Helena Rubinstein, Surrealist Mascara & Liner, date published Nov. 2006; www.gnpd.com, 2 pages.
Invima, Isadora Wonder Full Mascara, date published Sep. 2006; www.gnpd.com, 2 pages.
Kao, Aube Couture, Designing Double Mascara, date published Dec. 2008; www.gnpd.com, 3 pages.
Isehan, Kiss Me Mascara Remover, date published Sep. 2008; wwww.gnpd.com, 2 pages.
Kose, Fasio Easy Mascara Remover, date published Jun. 2009; wwww.gnpd.com, 3 pages.
Kose, Fasio Mascara Easy Remover, date published Jan. 2009; wwww.gnpd.com, 2 pages.
Lorac Cosmetics, Lorac, Fairytale Life Makeup Collection, date published Dec. 2007; www.gnpd.com; 4 pages.
L'Oréal Double Mascara, Date published May 2006; www.gnpd.com, 2 pages.
MAQuillAGE Shisiedo, Mascara Remover, date published Jun. 2008; wwww.gnpd.com, 2 pages.
Napoleon Perdis Cosmetics, NP Set Eyeliner, date published Mar. 2009; www.gnpd.com, 4 pages.
Napoleon Perdis Cosmetics, NP Set, Eye Palette, date published Feb. 2009 www.gnpd.com, 3 pages.
Prestige Cosmetics, Glitter Lash Mascara, date published Dec. 2008, www.gnpd.com, 2 pages.
Revlon, Limited Edition Dual Lash Mystique Mascara, date published Jun. 2003; www.gnpd.com, 1 page.
Rimmel, Coty, Volume Extend Waterproof Mascara, date published Sep. 2006; www.gnpd.com, 2 pages.
Rimmel, Double Play Multi Look Mascara, date published Apr. 2007; Mar. 2007; www.gnpd.com, 2 pages.
Rossman, Rival de Loop Young, Double Brush Mascara, date published: Oct. 2009; www.gnpd.com, 2 pages.
Shiseido, The Makeup Eraser Pencil, date published Jun. 2001; wwww.gnpd.com, 2 pages.
Sleek Makeup, Duo Dip It Mascara+Eyeliner, date published Mar. 27, 2009; www.gnpd.com, 3 pages.

(56) References Cited

OTHER PUBLICATIONS

SmashBox Limitless Lash Mascara, date published May 2003 wwww.gnpd.com, 2 pages.
Swab Plus Eye Makeup Remover Swabs, date published Nov. 2007; wwww.gnpd.com, 2 pages.
SwabPlus Waterproof Mascara Remover Swabs, date published Dec. 2002; wwww.gnpd.com, 2 pages.
Tarte Cosmetics, Tarte Fall 2008, Eye Couture Day-to-Night Eye Palette, date published Aug. 2008; www.gnpd.com, 2 pages.
The Art of Makeup, VIP Complete Cosmetic Kit, date published Feb. 2008; www.gnpd.com 4 pages.
Narus Cosmetics, Wink Up Mascara Remover, date published Mar. 1999; wwww.gnpd.com, 1 page.
Xtreme Color, Mary-Kate and Ashley, Eye Drama Creme Eye Color Plus Rich Mascara, date published Jul. 2004; wwww.gnpd.com, 2 pages.

\* cited by examiner

1720

1730 h = 1 pixel

Thickness of Individual lash = X number of pixels

1740

MASCARA AND APPLICATOR

CROSS REFERENCE TO RELATED APPLICATION

This application claims the benefit of U.S. Provisional Application Ser. No. 61/487,149, filed May 17, 2011.

FIELD OF THE INVENTION

The present application is directed, generally, to a long-wear mascara product including an applicator for applying the mascara. Specifically, there is disclosed a long-wear mascara formula in combination with a twisted-wire applicator that provides an improved aesthetic benefit to the eyelashes of a user when the mascara is applied with the applicator.

BACKGROUND OF THE INVENTION

Mascara compositions have been used for many years to increase the thickness, length and overall aesthetic appearance of human eyelashes. There are generally two types of mascara: regular and water-resistant/waterproof. Regular mascara is generally water soluble, while the water resistant variety is typically removable with soap and water. Over the course of a day, conventional mascaras typically wear off relatively quickly, especially when subjected to physical abrasion, and reapplication during the day may be necessary. But reapplying mascara over the course of a day may be undesirable for a user. As a result, these users may sacrifice the look they desire because they simply do not have the time or the desire or continually reapply mascara. In addition, even though conventional mascara typically wears off over the course of the day, a small amount may remain at the end of the day when the user goes to sleep. If this small amount of mascara remaining on the eyelashes at night is not removed, it may be undesirably transferred onto a sleeping surface (e.g., pillows, sheets, covers, bed clothes).

"Long Wear" mascaras are known, and may overcome some of the issues related to maintaining a "newly applied mascara" look throughout the day without the drawbacks of reapplication. But "long" is a relative term, and while existing long wear mascaras are intended to reduce or eliminate reapplication throughout the day, they are generally not suitable for multi-day wear. Some conventional long wear mascaras may not even provide a suitable look for 24 hours. One problem associated with at least some conventional long wear mascaras is that the composition must be sufficiently tacky to stay on the lashes for an extended period of time, but the thicker, tackier mascara may result in the appearance of undesirable "clumps."

Mascara compositions are generally applied using an applicator, sometimes referred to as a mascara brush or comb. When using a brush, the mascara is typically removed from a reservoir by placing the brush in the mascara reservoir and removing it. Excess mascara is removed from the brush with a wiper that contacts the distal ends of the bristles of the mascara brush as the brush is removed from the reservoir. The mascara that remains on the brush tends to be disposed around the core of the brush or flow toward the core. When the brush is contacted with the eyelashes of a user, the bristles separate the eyelashes such that the separated eyelashes can come into contact the core of the brush to receive the mascara disposed thereon.

There are generally two types of mascara brushes: molded plastic brushes and twisted-wire brushes. Plastic molded brushes are commonly formed from a thermoplastic material in an injection mold or similar process. Molded brushes typically have bristles arranged uniformly in rows with relatively wide spaces between the bristles. Mascaras having a relatively higher viscosity, such as some conventional long-wear mascaras, work well with a molded plastic brush for high levels of look control because the larger spaces between the bristles of the molded plastic brush are suitable for receiving the thicker composition (i.e., the composition flows more easily between the bristles). In contrast to a molded plastic brush, the bristles of a twisted-wire brush are generally spaced more closely together, and generally do not form well defined rows. This reduced space between bristles results in more resistance to flow for a higher viscosity mascara composition. Twisted-wire brushes are typically formed by placing a plurality of bristles between two parallel metal wires and then twisting the wires together in a helical or helix-like (e.g., coiled or spiral) configuration to trap and hold the bristles between the wires. It is not uncommon for the bristles of a twisted-wire brush to appear to be randomly distributed on the core.

According it would be desirable to provide a mascara product that lasts more than 24 hours and achieves the desired look of current mascaras and the consumer desired feel, and can be applied with a twisted-wire brush.

SUMMARY OF THE INVENTION

Figure 1:
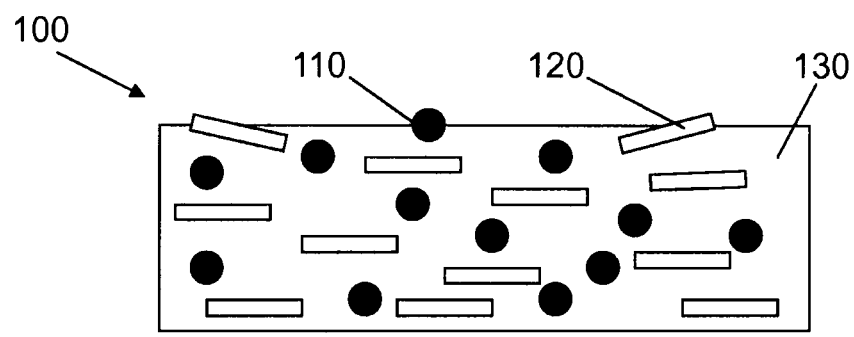
FIG. 1 is a plan view of an illustration of a film structure.

In order to provide a solution to the aforementioned problems, disclosed herein is a semi-permanent mascara product comprising a container for storing a supply of semi-permanent mascara composition and a supply of semi-permanent mascara composition disposed in the container. The supply of semi-permanent mascara composition disposed in the container includes from 1-60% by weight of a colorant, from 10-80% by weight of a carrier, and from 15-35% of a film former selected from the group consisting of tall oil glycerides, pentaerythrityl rosinate, glyceryl rosinate, hydrogenated versions of these and mixtures thereof. The semi-permanent mascara product also includes an applicator for receiving the mascara composition and applying the mascara composition to a keratinous surface. The applicator includes a core and a plurality of fiber bristles joined thereto and extending outwardly therefrom. The applicator also includes a handle and a stem dispose between the handle and the core. The handle is removably and reattachably joined to the container such that the core contacts the mascara composition when the handle is joined to the container.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

DEFINITIONS

"Joined" means configurations whereby an element is directly secured to another element by affixing the element directly to the other element, and configurations whereby an element is indirectly secured to another element by affixing the element to intermediate member(s) that in turn are affixed to the other element.

"Keratinous tissue," means keratin-containing tissue layers disposed as the outermost protective covering of mammals which includes, but is not limited to, skin, hair, and nails.'

"Mascara" and "mascara composition" mean a liquid cosmetic composition that is applied to eyelashes to provide an aesthetic benefit or change in appearance such as, for example, the appearance of a color change, a volume change, and/or a length change. Mascara may also be applied to eyelids, and/or eyebrows. The present mascara compositions are formulated for topical application to mammalian keratinous tissue for use in cosmetic products. The methods of using mascara compositions are also included within the meaning of mascara composition.

"Twisted-wire brush" means a brush for applying mascara to the eyelashes of a person characterized by a plurality of bristles securely held between at least two wire-shaped elements coiled around one another in a helical, helix-like, or braided configuration.

Semi-Permanent Mascara Composition

Disclosed herein is a semi-permanent mascara formula that remains intact on the eyelashes and/or eyelids of the wearer for greater than 24 hours (e.g., 36 hours or more or even 48 hours or more), but typically less than five days. Conventional mascara formulations include a large amount of wax(es) (5-15%) and iron oxides (6-12%) while using relatively small amounts of film forming polymers (4-8%). The films formed by conventions mascara compositions are generally defined by the waxes present in the composition, which can have crystal sizes in excess of 20 microns and appear jagged and rough when viewed under magnification. The pigments used in conventional mascaras may also have a relatively large particle size, for example, widely distributed in the 2-5 micron range. It is known that the properties of a film are directly related to the volume concentration of solids it contains, which may be characterized by the concept of critical pigment volume concentration ("CPVC"). The CPCV is the point at which there is just enough film-former matrix to wet and fill the voids between individual particles. At solids volume concentrations above the CPVC, the film-former matrix is no longer a continuous phase. Studies have shown that the pigment volume concentration impacts many film properties, including gloss, film flexibility and abrasion resistance. As the pigment volume concentration increases, film flexibility decreases and abrasion resistance remains the same or improves. When the CPVC is exceeded, the film will become brittle and abrasion resistance will decrease rapidly. Gloss also decreases as the pigment volume concentration increases and remains low when the CPVC is exceeded. Because conventional mascaras typically use pigment with relatively large particulates and a relatively low amount of polymer, they tend to have a solids volume concentration in excess of the CPVC. As a result, conventional mascara films exhibit poor abrasion resistance and often are brittle films that flake easily.

The semi-permanent mascara compositions herein have a volume concentration of solids that is below the CPVC. This may be achieved in two ways. First, using only small particle size solids for both the pigments and thickeners, for example, using a thickener of only disteardimonium hectorite clay particles (D90<10 microns) at from 10% to 15% by weight of the semi-permanent mascara composition, and a pigment formed from jet milled iron oxide particles (D90<1 micron) present at from 7% to 10% by weight of the composition. It is believed, without being limited by theory, that minimizing the size of all particulates in the system may increase the CPVC of the semi-permanent new mascara technology above that of conventional mascaras. Second, a greater level of film formers may be used (e.g., from 17 to 30%). Because the solids volume concentration of the film is below the CPVC, it generally exhibits greater resistance to flaking and transfer caused by stretching and abrading than conventional mascara compositions. Surprisingly, the present semi-permanent mascara composition forms a continuous film that provides a relatively smooth film surface with a glossy, dark appearance.

In addition to a suitable CPVC, it is important for the present semi-permanent mascara composition to have a suitable viscosity so that the proper applicator (i.e., brush), which is discussed in more detail hereinbelow, can be provided in a commercial product. Suitable viscosities are in the range of 50,000-800,000 centipoise ("cps"), 150,000-400,000 cps, or even 250,000-350,000 cps as measured by Brookfield brand RTV viscometer using a type TE spindle at 10 rpm and 25° C.

FIG. 1 illustrates an exemplary film 100 of the present semi-permanent mascara composition. The film 100 includes suitably spaced pigment particles 110 and thickener particles 120 dispersed in a matrix of film former(s) 130. The pigment particles may all be the same type and/or color of pigment or two or more different pigment types (e.g., organic and inorganic) and/or colors. Additionally or alternatively, the film 100 may include other types of colorants such as, for example, lakes and dyes. Similarly, the film 100 may include a single type of thickener (e.g., colloidal particles or wax) or two or more different types of thickeners. The film 100 may be formed from an anhydrous dispersion of pigment 110 and thickener 120 in a film-former matrix 130, along with one or more volatile carriers. One particularly suitable example of a semi-permanent mascara composition for use herein is formed as an anhydrous dispersion of rosin esters as film formers, iron oxides as colorants, and isododecane as a volatile carrier. In this example, it may be desirable to also include a clay network (e.g., bentone clay) to stabilize the matrix.

Figure 2:
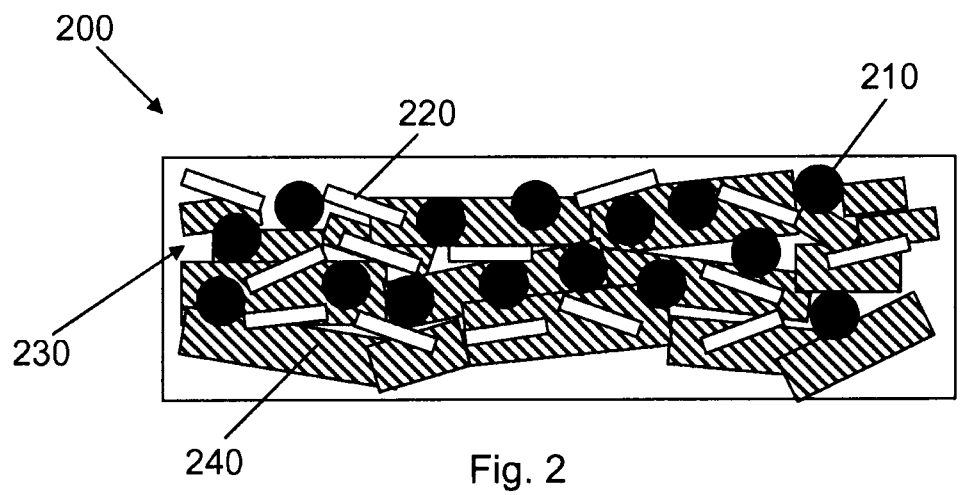
FIG. 2 is a plan view of an illustration of a film structure.

FIG. 2 illustrates a film 200 formed from a conventional mascara composition. The conventional film 200 includes spaced pigment particles 210 and thickener particles 220 dispersed in a matrix of film formers 230. But unlike the film 100 illustrated in FIG. 1, the conventional film 200 also includes relatively large wax particles 240 disposed in the matrix, which impart undesirable characteristics to the film 200.

Film-Former

The present semi-permanent mascara composition includes a film-former. Suitable film formers include rosin esters, which are derived from rosin. Rosin is a solid form of resin obtained from conifers (e.g., pine tree sap). Rosin is known to include a mixture of closely related rosin acids, especially abietic acid, characterized by three fused six-carbon rings, C=C double bonds that vary in number and location, and a single carboxylic acid group. Commercial methods for obtaining rosin are also known and include, e.g., distilling the volatile turpentine from oleoresin exuded from the wound of living pine trees to obtain gum rosin, or the chemical separation of tall oil, which is a byproduct of the wood pulp industry, to obtain tall oil rosin. The carboxylic acid group of a rosin acid can be converted to an ester by reacting the acid with an alcohol. Esterification of rosin modifies the softening point, adhesiveness, cohesiveness, and melted viscosity of the material. The alcohols typically used to make rosin esters are methanol, tri-ethylene-glycol, glycerol, and pentaerythritol. Tall oil rosin is esterified with glycerol to form tall oil glycerides, a mixture of rosin acids, and esters of glycerol. Tall oil glycerides are available from, for example, Arizona Chemical Co. Glyceryl rosinate, is the ester of a rosin acid reacted with glycerol. Pentaerythrityl rosinate, sometimes referred to as pentaerythritol rosinate, is the ester of a rosin acid reacted with pentaerythritol. Pentaerythritol rosinate is commonly used as a skin conditioning agent-emollient and viscosity increasing agent, and is nonaqueous in cosmetic formulations.

Rosin includes a conjugated system of C=C double bonds, which makes it susceptible to oxidation, isomerization and other chemical reactions. A common method to improve stability is to hydrogenate the rosin, for example, by the addition of hydrogen to the conjugated C=C double bonds in the presence of a catalyst to form saturated ring structures. Hydrogenated rosin esters have specific advantages over non-hydrogenated (e.g., lighter color, improved stability, and reduced skin sensitization). The hydrogenated versions of pentaerythrityl rosinate and glyceryl rosinate (i.e., pentaerythrityl hydrogenated rosinate ("PHR") and glyceryl hydrogenated rosinate ("GHR")) are suitable for use herein.

Film formers such as tall oil glycerides, pentaerythrityl rosinate, PHR, glyceryl rosinate, and GHR are used in the present semi-permanent mascara compositions in higher concentration than conventional mascara. The present semi-permanent mascara composition comprises at least 15%, 17%, or even at least 20%, but typically less than 50%, by weight, of a film former selected from the group consisting of tall oil glyceride, pentaerythrityl rosinate, glyceryl rosinate, and the hydrogenated versions and mixtures thereof. The ratio of film former to volatile carrier may be controlled such that the dried film consists of from 30% to 70%, 40% to 60%, or even 50% film former by weight.

Carrier

The semi-permanent mascara composition herein may include a carrier to help deliver the desired mascara components (e.g., pigments and film formers) to the eyelash or eyelid. In certain embodiments, the semi-permanent mascara composition may include a volatile carrier that quickly volatilizes from the surface of the eyelashes or eyelid, leaving the desired components behind. The volatile carrier may be present at 10% to 85%, 15% to 80%, or even 20% to 70% by weight based on the weight of the composition. Nonlimiting examples of suitable volatile carriers include volatile hydrocarbons, volatile silicones, and mixtures thereof.

Hydrocarbon oils suitable for use as a carrier in the present mascara compositions include those having boiling points in the range of 60-260° C., such as hydrocarbon oils having a carbon chain length of from C8 to C20 (e.g., C8 to C20 isoparaffins). Particularly suitable examples of isoparaffins include those selected from the group consisting of isododecane, isohexadecane, isoeicosane, 2,2,4-trimethylpentane, 2,3-dimethylhexane and mixtures thereof. Isodecane is available from Presperse under the brand name Permethyl 99A and has the formula: CH—$_3$(CH$_2$)10CH.

A volatile silicone fluid may also be used as a carrier herein. Suitable volatile silicone fluids include cyclomethicones having 3-, 4- and 5-member ring structures corresponding to the formula:

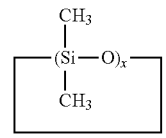

where X is from about 3 to about 6. Nonlimiting examples of commercially available volatile silicones include 244 Fluid, 344 Fluid and 245 Fluid, and/or 345 Fluid from Dow Corning Corporation.

Colorants

Colorants suitable for use in the present mascara compositions include, but are not limited to, dyes, pigments, lakes, and mixture thereof. (e.g., organic or inorganic pigments and colorants approved for use in eye-area cosmetics by CTFA and/or the FDA.) Exemplary inorganic pigments include particles of iron oxides (e.g., yellow, brown, red, black), titanium dioxides, iron sulfides, ultramarines, chromium oxides (e.g., green) or other conventional pigments used in cosmetic formulations. Examples of organic pigments include D&C Black No. 2, D&C Black No. 3, FD&C Red No. 40, D&C Green No. 5, FD&C Blue No. 1, and FD&C Yellow No. 5. Examples of lake dyes include various acid dyes which are laked with aluminum, calcium or barium. Additional colorants for use herein include annatto, caramel, carmine, β-carotene, bismuth oxychloride, ferric ammonium ferrocyanide, ferric ferrocyanide, chromium hydroxides (e.g., green), guanine, mica, aluminum powder, bronze powder, copper powder, manganese violet, zinc oxide. Suitable colorants along with their chemical structure are described in, e.g., 21 C.F.R. Part 74 and in the CTFA Cosmetic Ingredient Handbook, (1988), published by the Cosmetics, Toiletry and Fragrances Association, Inc. Other colorants may also be used as they are developed and determined safe.

Encapsulated colorant microparticles having average diameters of 0.1 to 10 microns may be acceptable for use in the present semi-permanent mascara compositions. Suitable examples of encapsulated colorant microparticles are disclosed in copending U.S. Publication Nos. 20090263658 and 20090271932A1. The encapsulated colorant microparticles may comprise from 1 to 60% by weight of at least one colorant, for example 5% to 40% or even 7% to 25% by weight.

Microencapsulated colorants may provide a more vibrant color to products used around the eye area, including eyelashes. The primary colors are understood to mean red, yellow and blue. An additional feature of microparticles is the elimination of milling or grinding often encountered with non-encapsulated colorants.

Colorants that are surface modified with a hydrophobic coating (e.g., triethoxycaprylsilane) may be acceptable for use herein. Hydrophobically coating colorants such as pigment particles may increase their dispensability in the non-polar solvent and increase their resistance to being washed off during exposure to showering and facial cleansing.

The semi-permanent mascara composition according to the invention comprises from about 0.1 to about 70% by weight, for example from about 0.5 to about 50% by weight, and especially from about 0.5 to about 35% by weight based on the total weight of the composition, of a colorant. Colorants in the form of particles having average diameters of 0.1 to 10 microns may be acceptable for use in the present compositions (e.g., 0.1 to 5 microns or even 0.1 to 1 microns). It may be desirable to select colorant particles with a diameter that is less than the thickness of the mascara composition dried-down film. The small size of the colorant particles may allow them to be fully encased in the dried film.

Thickeners

The semi-permanent mascara composition can be thickened or structured with colloidal particles and/or waxes. Thickeners for use in the present mascara compositions can be selected from the group consisting of waxes such as carnauba wax, candellila wax, beeswax, and polyethylene wax; particles such as disteardimonium hectorite, kaolin, silica, and magnesium carbonate; polymers; viscous hydrocarbons; and combinations thereof. Waxes are selected to maintain the film durability of the mascara composition. In some instances, the present semi-permanent mascara composition may include from 3-15% wax (e.g., from 4-10% or from 5-8%). In some instances, it may be desirable to include wax at an amount of less than 3.0%, for example, less than about 1.0% or eve less than 0.1%, by weight, of wax and wax like components. In some instances, the present mascara composition is free of wax.

Disteardimonium hectorite is a particularly suitable thickener to build structure/viscosity in the present mascara composition. This enables proper spreading/deposition across lashes, and ensures adequate stability/suspension of colorant particles in dispersion over time. It is preferable that the diameter of the disteardimonium hectorite is smaller than the thickness of the mascara composition dried-down film. The preferred diameter of the disteardimonium hectorite is less than 10 microns. The present semi-permanent mascara compositions may from about 1% to about 25% of suitable thickener such as disteardimonium hectorite, from about 2% to about 20%, or even from about 3% to about 15%.

Semi-Permanent Mascara Top Coat or Base Coat

It is to be appreciated that the semi-permanent mascara compositions described herein may be used in conjunction with another composition in a sequential application process. For example, the present semi-permanent mascara composition may be used as a top coat or base coat in a multi-step mascara regimen. Suitable examples of top coats and base coats are described in copending U.S. Ser. No. 13/274,852.

Actives

The compositions of the present mascara compositions may comprise a safe and effective amount of a biological, chemical, nutraceutical, or pharmaceutical active, or a combination thereof. Biological actives may include prostaglandins, antimicrobials, antibacterials, biocides, preservatives, proteins, amino acids, peptides, hormones, growth factors, enzymes (e.g., glutathione sulphydryl oxidase, transglutaminase), therapeutics, oligonucleotides, genetic materials (e.g., DNA, RNA), and combinations thereof. Chemical actives may include dyes, surfactants, sensates, hair conditioners, hair dyes, hair growth agents, hair removers, hair growth inhibitors, hair styling gels, and combinations thereof. Nutraceutical actives may include proteins, preservatives, vitamins, food-additive materials, and combinations thereof. Pharmaceutical actives may include antibiotics, drugs, hair growth agents, hair removers, hair growth inhibitors, and combinations thereof.

Oil Soluble or Oil Dispersible Additives

The choice of oil-soluble or dispersible additive and the amount present according to the invention will depend on the intended use of the composition and the effectiveness of the compound. In semi-permanent mascara, top coat and remover compositions, the oil-soluble or dispersible additive chosen is acceptable for skin and eye contact, as is well known to the skilled formulator. Suitable oil-soluble or dispersible additives are incorporated at levels generally between 1 and 20% by weight based on the weight of the matrix bead (equivalent to 90 to 300% on weight of the colorant). Preferably 5 to 15% by weight of the oil-soluble or dispersible additive is employed.

The oil-soluble or dispersible additive may include fatty alcohols such as Guerbet alcohols based on fatty alcohols having from 6 to 30, preferably from 10 to 20 carbon atoms including lauryl alcohol, cetyl alcohol, stearyl alcohol, cetearyl alcohol, oleyl alcohol, benzoates of $C_{12}$-$C_{15}$ alcohols, acetylated lanolin alcohol, etc. Especially suitable is stearyl alcohol. The oil-soluble or dispersible additive may include fatty acids such as Linear fatty acids of $C_6$-$C_{24}$, branched $C_6$-$C_{13}$ carboxylic acids, hydroxycarboxylic acids, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids). Further components that can be used are dicarboxylic acids of $C_2$-$C_{12}$, such as adipic acid, succinic acid, and maleic acid. Aromatic carboxylic acids, saturated and/or unsaturated, especially benzoic acid, can be used. Additional components that can be used as the oil soluble or dispersible additive include carboxylic acid salts; alkaline soaps of sodium, potassium and ammonium; metallic soaps of calcium or magnesium; organic basis soaps such as lauric, palmitic, stearic and oleic acid, etc., alkyl phosphates or phosphoric acid esters: acid phosphate, diethanolamine phosphate, potassium cetyl phosphate.

Other useful oil-soluble or dispersible additives comprise mild surfactants, super-fatting agents, consistency regulators, additional thickeners, polymers, stabilizers, biologically active ingredients, deodorizing active ingredients, anti-dandruff agents, film formers, swelling agents, UV light-protective factors, antioxidants, preservatives, insect repellents, solubilizers, colorants, bacteria-inhibiting agents, hair conditioning agents, vitamins, and the like.

Applicator

While a variety of conventional applicators are known in the art (e.g., molded plastic applicators and twisted-wire brush applicators), it has been surprisingly found that certain applicators provide an unexpected benefit of superior application of the present semi-permanent mascara. Conventional mascara compositions, especially conventional "long wear" mascaras, may act as a paste or semi-solid on the brush, rather than as a flowable liquid. Thus, the primary method of depositing such mascaras onto the mascara brush is by inserting the brush into a supply of mascara, typically contained in a bottle or similar container, so that the mascara is deposited on the head (i.e., bristles and core) of the brush. Excess mascara is removed from the head of the brush, especially the outermost portions of the bristles spaced away from the core, via a wiper when the brush is withdrawn from the mascara container. Ideally, a suitable amount of mascara remains at least on the core of the brush for application to the eyelashes of a user. When the brush is used as intended, the lashes of a user are moved past the bristles of the brush via the spaces between the bristles such that the lashes come into contact with the mascara-containing core and, optionally, portions of the bristles (e.g., the inner portions). Thus, it is the characteristics of the mascara (e.g., coherent strength & rigidity) in combination with the applicator and wiper that provides the primary mechanism of product control and dosing. Because conventional mascaras tend to be thick enough for the mascara to remain on the core of the brush, it is not uncommon for the spacing of the bristles to be determined primarily by the desired lash separation/clustering. But with the desire to provide lower viscosity mascaras, the spacing of the bristles becomes important for providing suitable product retention on the brush as well as the desired amount of lash separation/clustering. When using a lower viscosity formula such as the present semi-permanent mascara composition, which typically exhibit considerably more flow and lower cohesive structure/strength than conventional thicker mascaras, it is believed, without being limited by theory, that it is important for the brush bristles and/or inter-bristle spaces to provide suitable adhesion and capillary action to suitably retain the mascara on the brush head prior to application (e.g., no dripping, running, or pooling) and still provide the desired application experience (e.g., smooth, uniform application of mascara to the eyelashes).

Figure 9A:
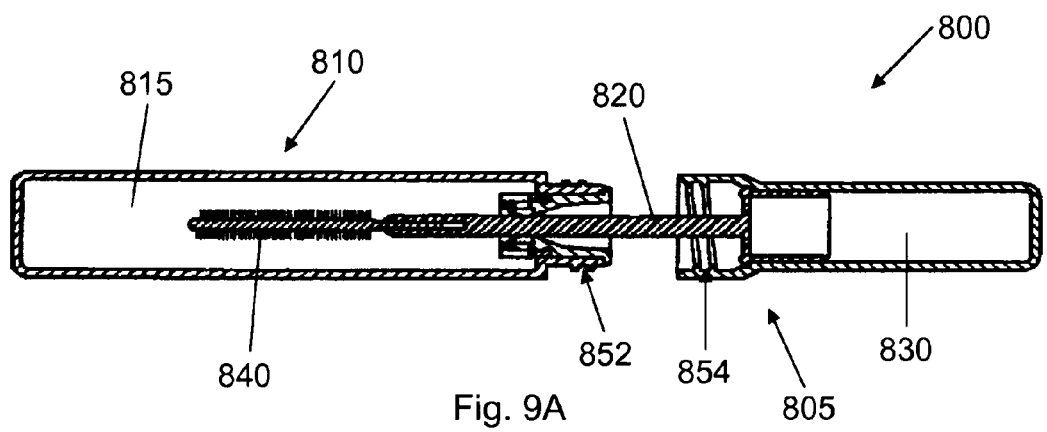
FIG. 9A is a plan view of a mascara package.

FIG. 9A shows an exemplary mascara package 800 for storing and dispensing mascara. The mascara package 800 may include a container 810 that defines an internal storage space or reservoir 815 for storing a supply of a liquid mascara composition. The mascara package 800 may also include an applicator 805 for transferring the mascara composition from the reservoir 815 to the eyelashes, eyebrows, and/or other keratinous tissue of a user. The applicator 805 may include an applicator head 840 that includes a core and a plurality of bristles, which are described in more detail hereinbelow. The applicator 805 may also include a handle 830, which is graspable by a user, and a stem 820 that joins the applicator head 840 to the handle 830. The mascara package 800 may include any suitable means for removably and reattachably joining the applicator 805 to the container 810 to provide a liquid impermeable container 800. For example, the container 810 may include mechanical threads 852 that are engageable with complementary threads 854 disposed on the applicator 805 to form a liquid impermeable barrier.

Figure 9B:
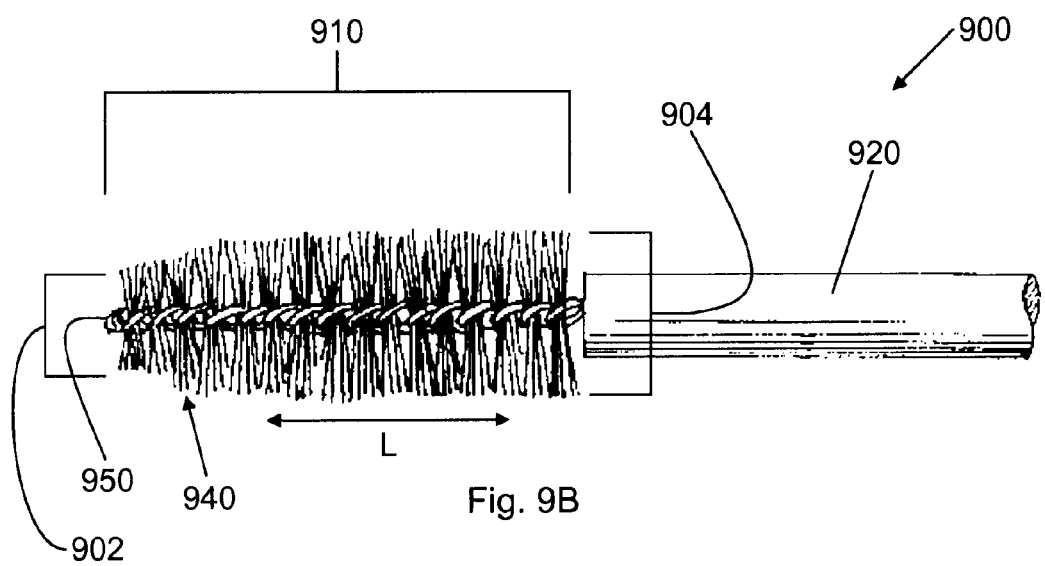
FIG. 9B is a plan view of twisted-wire brush.

FIG. 9B shows a twisted-wire brush applicator 900 suitable for use with the present semi-permanent mascara composition. The twisted-wire brush 900 includes an applicator head 910 joined to a stem 920, which may in turn be joined to a handle graspable by a user. The applicator head 910 includes a twisted-wire core 950 and a plurality of bristles 940 joined thereto and extending outwardly therefrom. The brush 900 has a minimum diameter 902 and a maximum diameter 904, which are defined by the lengths of the bristles when the applicator head 910 is viewed in a cross-section. The twisted-wire brush 900 may be include a plurality of bristles 940 (e.g., from 400 to 800 or any suitable number in this range) placed between two parallel wires, which are in a side-by-side, coplanar arrangement. Individual bristles 940 may be positioned in single-file between the wires, or groups of bristles 940 may be arranged in discrete clusters spaced apart from one another. The number and/or spacing of the bristles is important to provide sufficient capillary pressure to receive and hold the mascara composition on the core 950 of the applicator 900, but still allow the eyelash of the user to pass between the bristles 940 to contact the mascara disposed on the core 950. In addition, the number and/or spacing of the bristles 940 may be selected to provide desirable eyelash separation during use. The bristles 940 may be the same or different lengths and portions of the bristles 940 may extend lengthwise equidistantly out of the top and bottom surfaces of the plane defined by the parallel wires, or in any suitable proportional combination desired (e.g., 60/40 top/bottom; 70/30; 80/20; 90/10; or even 0/100). The parallel wires may then be coiled around one another to form a twisted-wire core 950 in which the plurality of bristles 940 are securely held.

The twisted wire brush 900 may include a twisted wire core 950 and/or brush head 910 having a length of between 15 and 32 mm (e.g., between 24 and 26 mm). The twisted wire core 950 may have between 10 and 30 turns (e.g., 17 to 19) and/or between 0.6 and 1.0 turns/mm (e.g., 0.66 to 0.77). The applicator head 910 may have a uniform cross-section or a non-uniform cross-section. The bristles 940 may be solid, hollow, or a combination thereof. The bristles 940 may have the same or different lengths, for example, between 2.5 and 7 mm. The core 950 and bristles 940 may be formed from any suitable material known in the art. For example, the core 950 may be formed from aluminum wires and the bristles 940 may be formed from a natural or synthetic fibrous material such as plant fiber or polypropylene fibers. It is to be appreciated that while fibrous bristles 940 may be formed from thermoplastic materials such as polypropylene, they do not include bristles that are formed in well-known injection molding processes (or other similar processes), wherein one or more molten thermoplastic materials are used to form the bristles and core of the brush as a unitary structure or to form the bristles as a sleeve that is placed over the core. Suitable examples of materials for making a twisted-wire core 950 and bristles 940 are disclosed in U.S. Pat. No. 5,490,529 to Karl, filed Jan. 18, 1994.

Twisted-wire brushes suitable for use with the present semi-permanent mascara composition provide good lash separation without undesirable "clumping." Without being limited by theory, clumping is commonly perceived by consumers as the main failure mechanism of a mascara product, and generally occurs when the mascara product causes individual eyelashes to stick together and form clumps. Clumping at the base of eyelash may be acceptable to some consumers, but clumping at other portions of the eyelash, especially the outer end portion, is generally unacceptable. Separation, as the name implies, is the perception by a consumer that the individual eyelashes are discernible such that they exhibit the length, curl, and/or volume beauty benefit desired from the mascara product. Thus, a mascara product may cause some clumping at the base of the eyelash, but if there is good separation acceptable beauty benefits may still be obtained. Clumping may be quantitatively measured according to the Weighted Average Thickness (W.A.T.) Test described in more detail below and in co-pending U.S. Provisional Ser. No.

61/646,941. Suitable W.A.T. values after five stokes include values of less than 30, 27 or even less than 25, when measured according to the W.A.T. test.

Figure 10A:
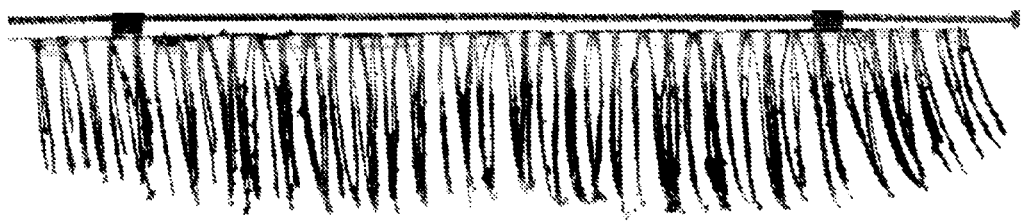
FIGS. 10A and 10B show a fake eyelash with an exemplary semi-permanent mascara composition thereon.
Figure 10B:

FIGS. 10A and 10B illustrate the effect of mascara formulation and brush combinations on clumping and separation. An exemplary semi-permanent mascara was applied to the artificial eyelashes in FIG. 10A with a suitable twisted wire brush. The same exemplary semi-permanent mascara was applied to the artificial eyelashes shown in FIG. 10B with a conventional molded plastic brush. The eyelashes in FIG. 10A exhibit improved separation and less clumping compared to the eyelashes illustrated in FIG. 10B.

While some of the foregoing disclosure and examples may describe a twisted-wire brush applicator, it is to be appreciated that other types of mascara applicators (e.g., molded plastic brush type applicators) may be suitable as well, provided such applicators are able to suitably separate a user's eyelashes and minimize or even prevent clumping. Additionally, such other types of applicators must have suitable bristles, inter-bristle spaces, and/or a core for providing the capillary pressure and/or adhesion necessary to prevent a relatively low viscosity, semi-permanent mascara composition from undesirably running, dripping, or pooling prior to application of the mascara to the eyelashes.

A suitable mascara product according to the present disclosure includes a container (e.g., bottle or the like) for storing a supply of the present semi-permanent mascara composition; an applicator (e.g., twisted-wire brush) for transferring mascara from the container to the eyelashes of a user; and a supply of the present semi-permanent mascara composition disposed in the container. The applicator may include a handle which is removably and/or reattachably joined to the container (e.g., with screw threads, snap collar, or the like).

Test Methods

Rub Test
Equipment:
Smooth substrate for supporting the film for testing (e.g., 10"×5½" Leneta Form 2A Opacity Chart)
0.006" draw down bar
Draw down board (i.e., hard, flat surface suitable for supporting the Leneta chart and ample).
White paper towel (or similar substrate) with sufficient strength to withstand test (e.g., WypAll L40 brand paper towels available from the Kimberly-Clark Corporation)
2½" diameter 2 kg weight
2½" diameter arch punch
Scissors
50° C. Oven
Double sided tape
Spectrophotometer (e.g., Datacolor Microflash 200d)
Procedure:
1. Drawdown Preparation:
   a. Place a Leneta card on a drawdown board, Black/White side up. Label the top right of the card with sufficient sample & solvent identification. Take care to touch the card as little as possible since skin oils can affect the film thickness of product on the card.
   b. Apply 1-2 ml of product in a line across the top of the card, and use a 0.006" drawdown bar to draw a film down the entire length of the card.
   c. Repeat steps 1a & 1b for all products to be tested.
   d. Once all draw downs have been completed, place them in a 50° C. oven for two hours. Take care not to mar the film surfaces.
   e. After an hour, remove the samples from the oven and allow them to equilibrate to ambient room temperature.
2. Sample Abrasion:
   a. Use an arch punch to punch out 2½" diameter "abrasion substrate" disks from "WypAll" paper towels.
   b. Completely and evenly, (do not overlap) apply strips of double sided tape to the bottom of a 2 kg weight. Cut away excess tape that extends beyond the perimeter of the weight bottom. Place and adhere a single WypAll disk (1 ply thickness) to the sticky bottom of the weight. This will be used to abrade the film and see how much of it is removed.
   c. Place the disk/weight in the center of the first 3"×3" testing area. Twist the disk through two full revolutions in ⅛ revolution increments. Carefully remove the weight (up and away from the drawdown), and remove the abrading disk from the bottom of the weight. (Only change the double sided tape when a disk will no longer firmly adhere to the bottom of the weight.)
   d. Perform steps 3a, 3b, & 3c for all subsequent Leneta card drawdowns.
3. Color Measurement.
   The procedure below is described by using a Datacolor Microflash 200d brand spectrophotometer, but one of ordinary skill in the art will appreciate that other spectrophotometer capable of measuring a Delta L value on the L*C*h color scale may be equally suitable.
   a. Turn on the spectrophotometer.
   b. Press the 'Menu' key on the front of the spectrophotometer until the word "Set-up" appears.
   c. Click the button directly below the word "set-up" to select the set-up menu.
   d. Use the arrow keys to pick the calibration program.
   e. Set the 'hand-held head' to Specular Included. (Using the toggles on the head, confirm that "white" (vs black) is showing through port.)
   f. The calibration program prompts you to place the white tile under the spectrophotometer head and press the trigger.
   g. The prompt that instructs you to measure the Black Trap. Place the black trap under the head and squeeze the trigger.
   h. The calibration is now complete.
   i. Using the toggles on the back of the spectrophotometer's hand-held head, set the Specular to "Excluded". (Confirm that "black" is showing through the port.)
   j. Select 'Illuminant' from the Main Menu. Use the D65/10 setting.
   k. Select Display from the main menu. Select CIE LCH Data and choose add.
   l. To take measurements, press the large Menu Key on the front of the spectrophotometer.
   m. Select 'STD' from the menu. Select 'Temporary Standard'. Place the spectrophotometer over an unused abrasive disc over the white section of an unused Leneta card and take a reading by squeezing the trigger. This measurement is now set as the standard.
   n. Place an abrasive disc that has abraded a product film over the white section of an unused Leneta card then place the spectrophotometer over the disk and take a reading by squeezing the trigger.
   o. Record the Delta L value. Take 2 additional measurements of the sample, measuring a different area of the disk each time. The reported result for the test is the absolute value of the average of the 3 measurements.

Weighted Average Thickness (W.A.T.) Test

Mascaras tend to coat lashes differently depending on the combination of formula and brush (e.g., the size of the brush and/or configuration of the bristles). In some instances, a user may dump mascara at the base of the lashes upon first contact of the brush with the lash and only a small amount of mascara is moved along the shaft of the lashes to the tips. This may result in an undesirable difference between the increases in thickness at the base of the lash versus the tip of the lash. That is, the volume benefit that some users desire may not appear to be evenly distributed along the lash. In some instances, the mascara brush may be more effective at coating the eyelashes disposed near the center portion of the eyelid versus the eyelashes disposed near the edge(s). This may depend on the ability of the brush to hold the mascara along the entire length of its core. Mascara brushes that load in the center of the core but not at the tip will give inconsistent coating from one end of the eyelash array to the other. Thus, it is important to measure mascara deposition in terms of lash thickness transformation across all lashes in order to map an accurate picture of their performance efficacy.

The W.A.T. Test provides a method to reproduce the effect of applying mascara compositions to eye-lashes and quantifying certain qualitative mascara effects on lashes. In particular, the W.A.T. test may be used to quantify the clumping characteristics associated with applying mascara to eyelashes. Even more particularly, the W.A.T. test may be used to illustrate the reduced clumping benefit provided by the present mascara formula when used in conjunction with a twisted wire brush. The W.A.T. value of an eyelash may be measured after applying mascara with one or more strokes (e.g., 1, 2, 3, 4, 5, 6, 7, 8, 9 or 10). It is believed, without being limited by theory, that five strokes may be of particular interest because it corresponds to the "beauty end state." That is, it is believed that the typical user of mascara moves the applicator along the length of the eyelashes five times when applying mascara. However, W.A.T. values at 1 stroke and 3 strokes or other numbers of strokes may also be helpful when evaluating the clumping characteristics of a mascara formulation, especially regarding "dump and fix" type mascara use. Dump and fix generally means applying a dose of mascara to the eyelash on the first stroke ("dump") and using subsequent strokes to obtain a desired look ("fix"), for example, by distributing the mascara homogenously along the length of the eyelash. Dumping the mascara typically results in high clumping, and the subsequent fixing is important to understand how well the mascara and brush combination reduce undesirable clumping. In particular, the change in W.A.T. value between the first and third stroke, the first and fifth strokes, or even the third and fifth stroke may provide an important indication of how well the composition and brush combination reduces clumping.

Figure 15:
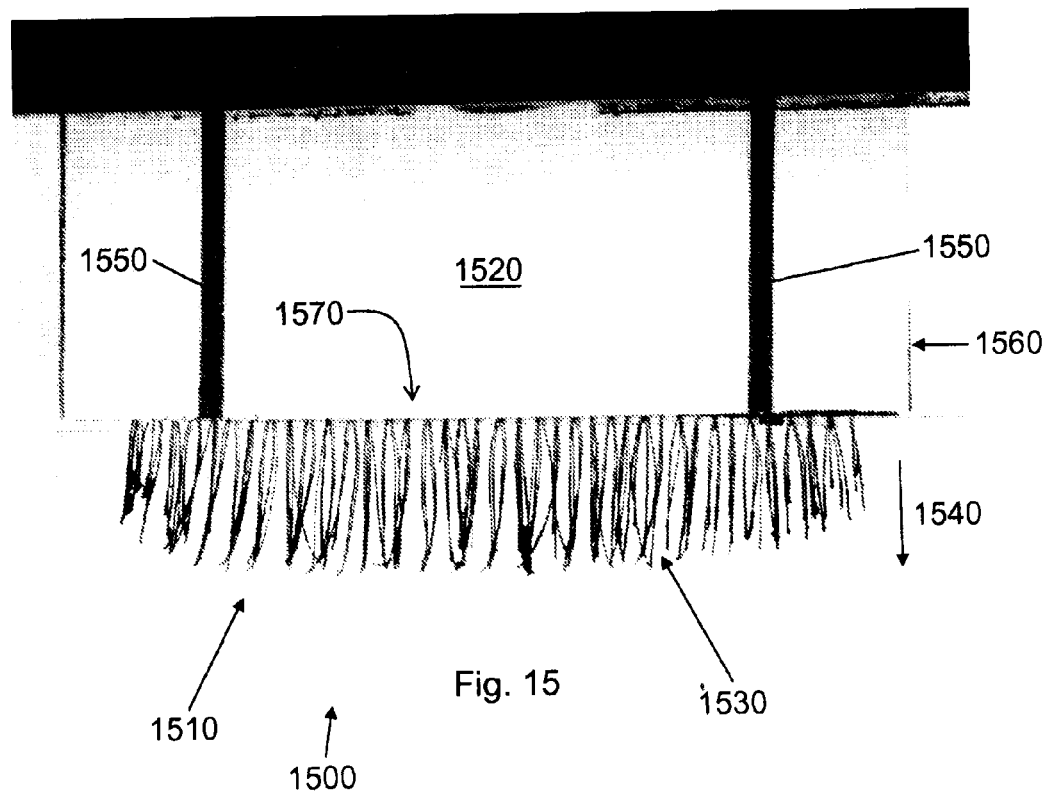
FIG. 15 is a captured image an eyelash substrate joined to a reposition template for use in the W.A.T. test.

Materials and Equipment:
Suitable eyelash substrate that represents the thickness and length of a typical human eyelash (e.g., Ardell 109 brand Fashion Lashes, which are made of natural human hair),
White paper or card material. The paper or card material should be selected to have suitable size and rigidity to support the eyelash substrate, and should provide suitable contrast between the eyelash and the background when the sample is photographed.
DSLR camera 7 megapixel or higher.
A clamp to hold the samples in place for imaging.
4 spot lights—5000-5500K (2 each side of the sample).
standardized rig to hold a camera at a fixed distance directly above the lighting and the sample.
laptop computer configured to interface with the camera.
Suitable image analysis software capable of repositioning and pixel based contrast analysis post image capture (e.g., image J software).
Procedure:

FIG. 15 shows a captured image 1500 of an eyelash substrate 1510 affixed to repositioning template 1520. Referring to FIG. 15, a clean, undamaged eyelash substrate 1510 (i.e., no bent or misshapen eyelashes) is attached to a repositioning template 1520 made from a white paper or card material cut to 4 cm×4 cm. The repositioning template 1520 is used to help ensure that the base 1570 of the eyelash substrate 1510 is substantially straight, as opposed to the arc it may naturally be bent in. Thus, the eyelashes in the eyelash substrate 1510 should all point in substantially the same direction for analysis, as indicated by the arrow 1540. A black tram line 1550 is provided (e.g., with a suitable black marker or pen) 1 cm from each outer edge 1560 of the repositioning template 1520, as shown in FIG. 15. The tram lines 1550 are positioned just inside the lash array space and act as "anchor points" for the ghosting software, which is described in more detail below.

Once the lashes are attached to the template 1520 and all lashes are pointing in substantially the same direction, mascara is applied to the eyelashes in a fixed dosing pattern: 1 stroke, 3 strokes, and 5 strokes to show the loading effect on the lashes and mascara deposition efficiency (i.e. building physical volume per lash without creating clumps). Each stroke requires two brush/lash interactions or swipes to contact all of the eyelashes of the eyelash substrate 1510 (i.e., one swipe from the left side and one from the right side). The $1^{st}$, $3^{rd}$ and $5^{th}$ stroke data are believed to be particularly important for determining the degree of user satisfaction, as this corresponds to the number of strokes commonly used by a person when applying mascara.

To apply the mascara to the eyelashes of the eyelash substrate 1510, remove the mascara applicator carefully from the mascara package by pulling the brush and wand directly outwards (i.e., do not "pump" the pack) and discard any globs of mascara present on the tip of the brush (e.g., using a tissue). Hold the edge of the template 1520 such that the eyelashes point away from you at a downward angle of 45 degrees. Hold the brush perpendicularly to the lashes proximate the base 1570 of the eyelash substrate 1510. Contact the mascara brush with the eyelashes at the base 1570 and move the brush along the length of the eyelashes 1530 in a continuous, uniform motion towards the tip 1530 of the eyelashes. It should take approximately 1-2 seconds to move the brush along the length of the eyelashes from the base 1570 to the tips 1530. During application, the brush may be rotated one quarter of a turn as it reaches the tips 1530 of the eyelashes. Perform the application process for both the left and right sides of the eyelash substrate 1510. For each subsequent stroke after the first, do not add additional product onto the applicator brush. In addition, during application, the brush should not be rolled or tilted along the lashes in a way that increases the application pressure or alters the application speed.

Figure 16A:
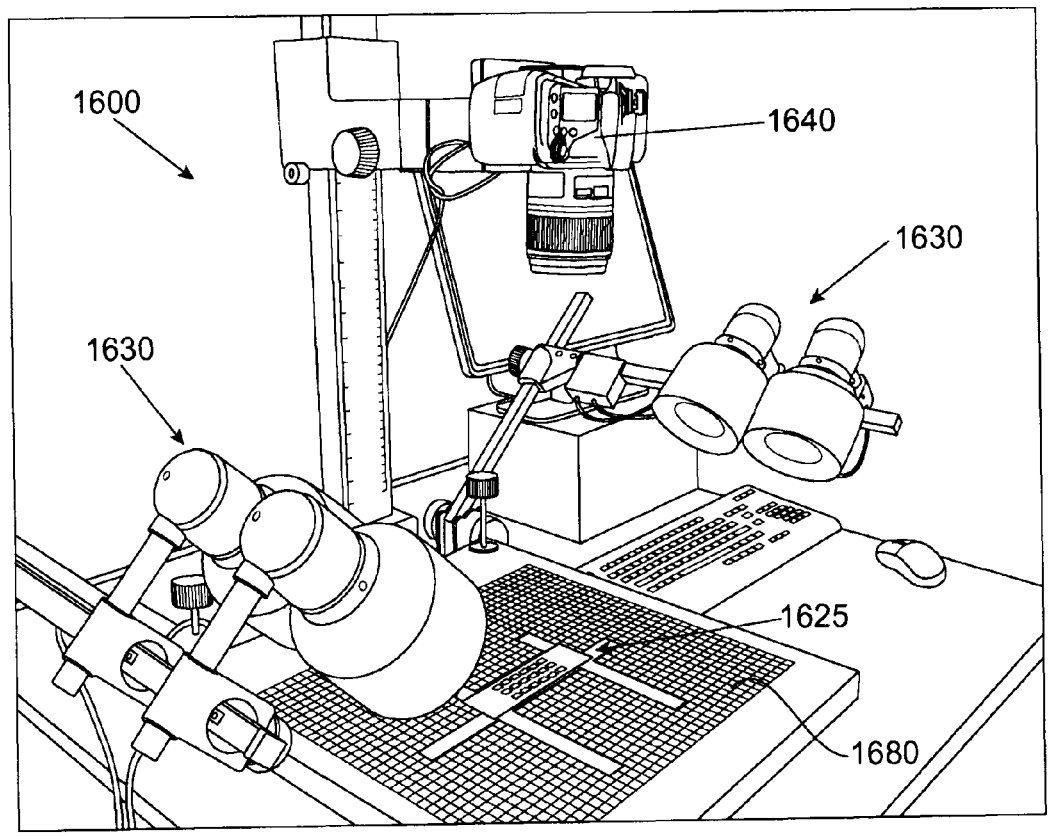
FIGS. 16A-16C are photographs of an imaging rig.
Figure 16B:
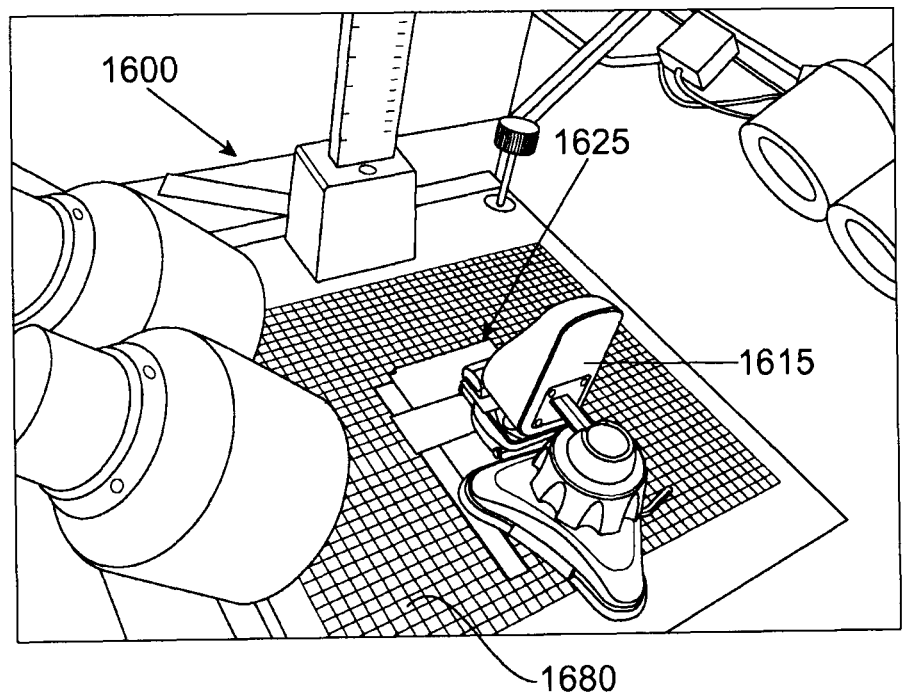
Figure 16C:
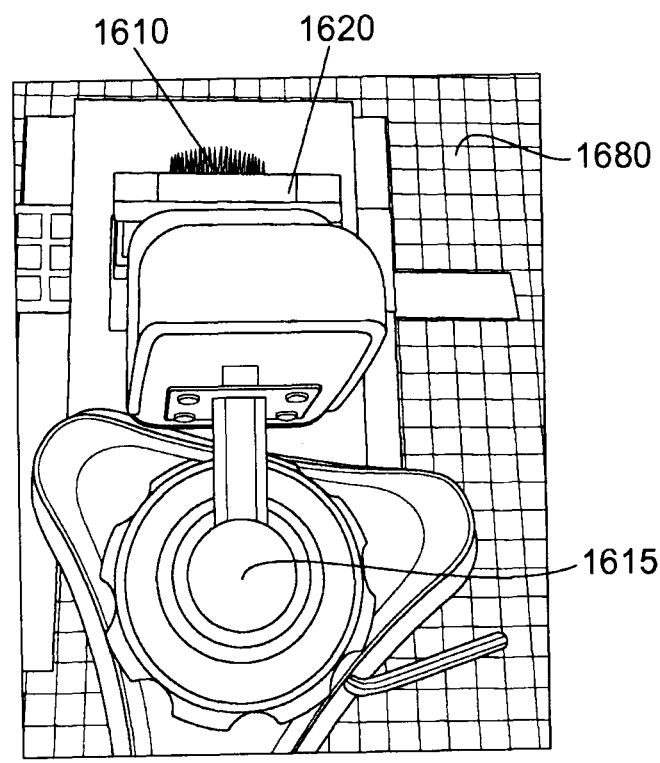

FIG. 16A illustrates an exemplary imaging rig 1600 suitable for use in capturing an image of the eyelash substrate for analysis. The imaging rig 1600 includes a rigid horizontal surface 1680 suitable for supporting a repositioning template 1620 in combination with an eyelash substrate 1610. The imaging rig 1600 also includes one or more lights 1630 and a camera 1640 positioned to capture an image within a target image area 1625. The target image area 1625 should be sized to completely contain the repositioning template 1620 and eyelash substrate 1610, and should be positioned within the controlled lighting/camera setup to enable the camera 1640 to capture an image of the entire target image area 1625. FIG.

16B shows the repositioning template 1620, which includes the eyelash substrate 1610, secured to the horizontal surface 1680 of the imaging rig 1600 with a vice 1615. The repositioning template 1620 and the eyelash substrate 1610 are both positioned in the target image area 1625. FIG. 3C is a close-up view of the repositioning template 1620 secured to the horizontal surface 1680 of the imaging rig 1600.

Secure the repositioning template 1620 (to a suitable horizontal surface 1680 (e.g., with a vice 1615). Position the template 1610 within a controlled lighting/camera setup such that the camera 1640 will capture a suitable image of eyelash substrate joined to the template. It is important that the camera be capable of capturing an image with sufficient resolution for subsequent image analysis. In the exemplary setup in FIG. 16A, the camera 1640 may be positioned such that the lens is 48 cm above the target image area 1625, and lights 1630 are positioned on either side of the template to provide suitable illumination. It is also important that the camera 1640 include "ghosting technology," which is an imaging software program that typically comes with a DSLR-type camera. The ghosting function of the camera enables a user to capture an image and set it as a reference guide (i.e., the "ghost image"). This ghost image can be opened as a background to a "live" image (i.e., the captured image that is currently being viewed/analyzed), which enables a user to manipulate the position of the live image relative to the ghost image. A particularly suitable example of a camera 1640 is a Nikon D90 SLR brand camera, equipped with a 105 mm Macro Lens. It may be desirable to connect the camera to a computer equipped with suitable imaging analysis software such as, for example, ImageJ, which is an open-source, java-based image analysis program. Set the exposure time of the camera 1640 to ¼ second, the aperture to 32 and ISO to 200. Ensure that the camera is in focus and take a picture of the target image area.

Figure 17:
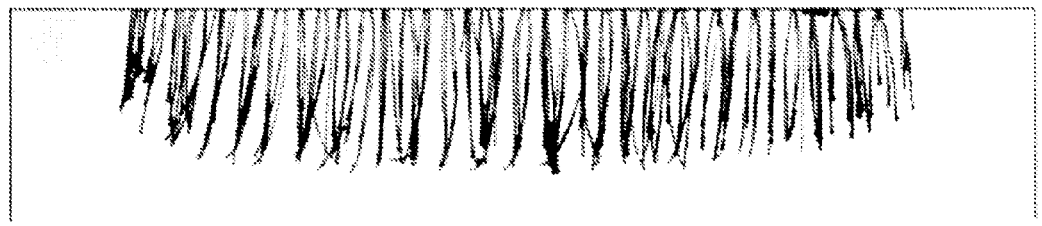
FIG. 17 shows the captured image of FIG. 15 after being cropped.
Figure 18:
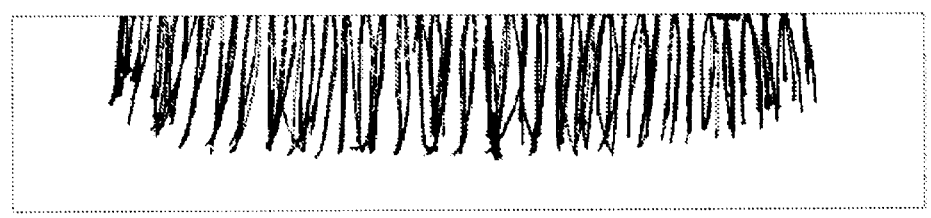
FIG. 18 shows the image of FIG. 17 after being converted to a binary image.
Figure 19:
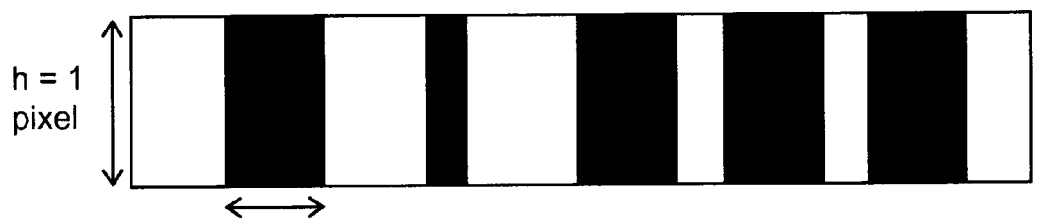
FIG. 19 shows a slice of the image of FIG. 18 after being converted into a barcode image by image analysis software.
Figure 20:
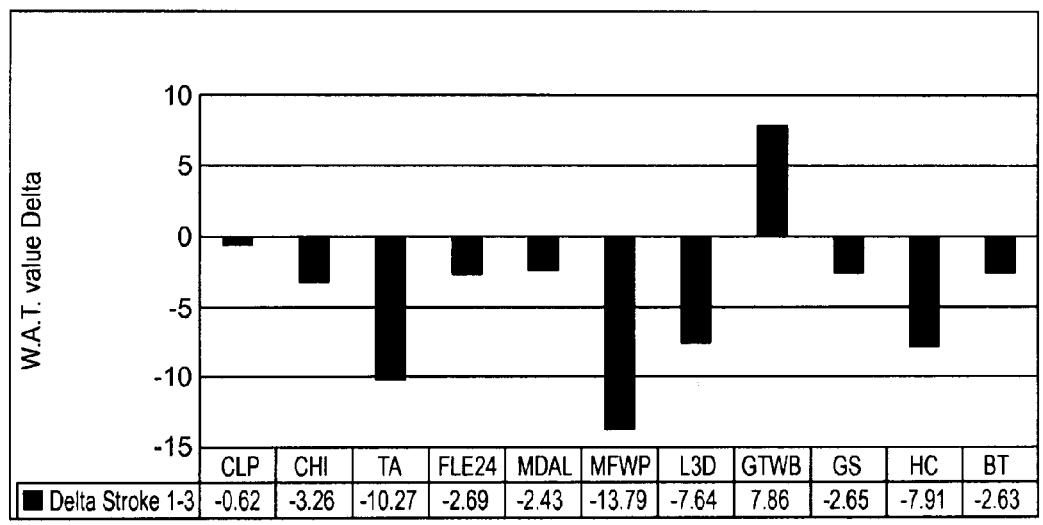
FIG. 20 illustrates the change in W.A.T. value from the first to the third stroke for a variety of mascaras.

Using the image analysis software, the captured image 1500 is cropped to provide a cropped image 1720, as illustrated in FIG. 17. The dimensions of the cropped image 1720 are determined from the repositioning template using the ghosting technology. Next, the cropped image 1720 is converted to a binary image 1730 (i.e., black and white), as illustrated in FIG. 18. The binary image 1730 is then separated or "sliced" into a plurality of 1 pixel high barcode images 1740 by the image analysis software, as illustrated in FIG. 19. Each slice is analyzed by the image analysis software for the number and thickness of each black region to generate output data, which is manipulated using programmable data analysis software such as Microsoft® Excel®. The data analysis software analyzes each black region and applies a weighting function to the thickness measurement, which identifies lashes which are changed by the mascara. The data analysis software should be programmed to allow for a bar code type data generation process. In other words, the data analysis software should draw imaginary lines for data collection across the total lash array at set widths—starting at the base of the eyelashes and finishing at the tips. Each slice of data is 1 pixel high and the lines of data are 10 pixels apart. Lashes which are not altered by the mascara product (e.g., same thickness as untreated) are not weighted. This is defined as those lashes with a thickness of less than 20 pixels. Lashes above 20 pixels are progressively weighted by the W.A.T. function:

$$Y = 0.0675x^2 - 23.75x + 225.$$

Where:
Y = the W.A.T. value for the eyelash array and
x = the thickness measurement The weighted thickness values are then used to calculate the Weighted Average Thickness value for the eyelash array by the analysis software. This procedure is repeated two more times and the average of the three W.A.T. values is calculated. A larger W.A.T. value corresponds to a higher clumping level, and consequently a more negative consumer perception or rating. Larger clumps are given a higher weighting than smaller clumps. Thus, one large clump will receive a higher W.A.T. value than two smaller ones.

EXAMPLE 1

A semi-permanent mascara composition as described herein may be made according to the method given directly below Table 1A using the ingredients and amount disclosed in Table 1A. The exemplary compositions in Table 1A are identified as prototypes 006, 017, 036 and 089.

TABLE 1A

Semi-Permanent Mascara Composition

| Phase | Material | Supplier/Trade Name | Function | 006 Wt % | 017 Wt % | 036 Wt % | 089 Wt % |
|---|---|---|---|---|---|---|---|
| A | Tall Oil Glycerides | Arizona Chemical Sylvagum RE 85K | Film Former | 12.5 | 8.5 | 12.5 | 12.5 |
| A | Pentaerythrityl Hydrogenated Rosinate | Eastman Foral 105-E | Film Former | 12.5 | 8.5 | 12.5 | 12.5 |
| A | 1,2 Hexanediol and Caprylyl Glycol | Symrise Symdiol 68 | Preservative | 1 | 1 | 1 | 1 |
| A | Isododecane | Presperse Permthyl 99A | Volatile Solvent | 45.88 | 53.88 | 50.50 | 45.88 |
| B | Disteardimonium Hectorite | Elementis Bentone 38V CG | Structurant | 14 | 14 | 14 | 14 |
| C | Propylene Carbonate | Huntsman Jeffsol | Polar Activator | 4.62 | 4.62 | — | 4.62 |
| D | Black Iron Oxide (Jet Milled) | Sensient Unipure Black LC 989 EM | Colorant | 9.5 | 9.5 | 9.5 | — |
| D | Triethoxycaprylsilane coated Black Iron Oxide (Jet Milled) | Sensient Unipure Black LC 989 EM AS | Colorant | — | — | — | 9.5 |
| TOTAL | | | | 100.000 | 100.000 | 100.000 | 100.00 |

Phase A ingredients are melted and mixed together with low shear mixing. Phase B is gradually added to the Phase A and then dispersed with high shear mixing. Phase C is then added and mixed in with high shear mixing. Phase D is then added and dispersed with high shear mixing. The batch is cooled to ambient conditions.

To demonstrate the superior performance of the new semi-permanent formula technology, the semi-permanent mascara composition of Table 1A was compared to several benchmarks selected from currently marketed mascara products. Benchmark products were selected for water resistant/waterproof, long wear, and semi-permanent stain product types. The comparative products are listed in Table 1B.

TABLE 1B

Comparative Mascara Products (benchmarks)

| Manufacturer | Mascara Name | Mascara Type |
| --- | --- | --- |
| Cover Girl ® | Lash Exact Waterproof | Waterproof |
| Cover Girl ® | Lash Exact | Water resistant |
| Maybelline ® | Define-A-Lash ® Waterproof | Waterproof |
| Maybelline ® | Define-A-Lash ® | Water resistant |
| Maybelline ® | XXL Pro 24 HR Bold ® | Water resistant/Waterproof |
| Tarte ® | 4 Day Stay Lash Stain | Semi-permanent Lash Stain |

The Cover Girl ® Lash Exact, Cover Girl ® Lash Exact Waterproof, Maybelline ® Define-A-Lash ®, and Maybelline ® Define-A-Lash ® Waterproof were selected because they have formulations that are typical of commercially available water resistant and waterproof mascara products. The Maybelline ® XXL Pro 24 HR Bold ® product was selected because it has the longest wear duration claim among commercially available long wear mascara products. The Tarte ® 4 Day Stay Lash Stain product was selected because it has the longest wear duration claim among commercially available semi-permanent lash stain products.

The products are evaluated in three ways: scanning electron microscopy to characterize the film morphology; technical testing to evaluate abrasion resistance; and a multi-day consumer usage test to assess wear performance in actual usage.

Scanning Electron Microscopy

Scanning electron microscopy (SEM) is used to compare the morphologies of mascara films applied to false lashes. A set of Ardell® 109 brand false eyelashes are trimmed to a length of approximately 0.95 cm and affixed to a metal bar. Five strokes of mascara are applied to a false eyelash sample using an automated mascara applicator device. The samples are allowed to dry completely. Individual lashes are removed from the metal bar and adhered to an SEM sample stub with carbon tape. The edges of the lashes are secured with silver paint. Samples are frozen in liquid nitrogen and then transferred to the Alto 2500 sample chamber to defrost at −95 C for 10 minutes. Samples are lightly coated with platinum before observation. Samples are observed using a Hitachi S4700 field emission SEM equipped with a Gatan Alto 2500 cryo stage and representative images are collected at −105 C in the cryo-SEM under the following conditions: kV=3 kV, $I_e$=10 μA, Mode=ultra high resolution, Detector=Mixed, Working Distance=~15 mm.

Figure 3:
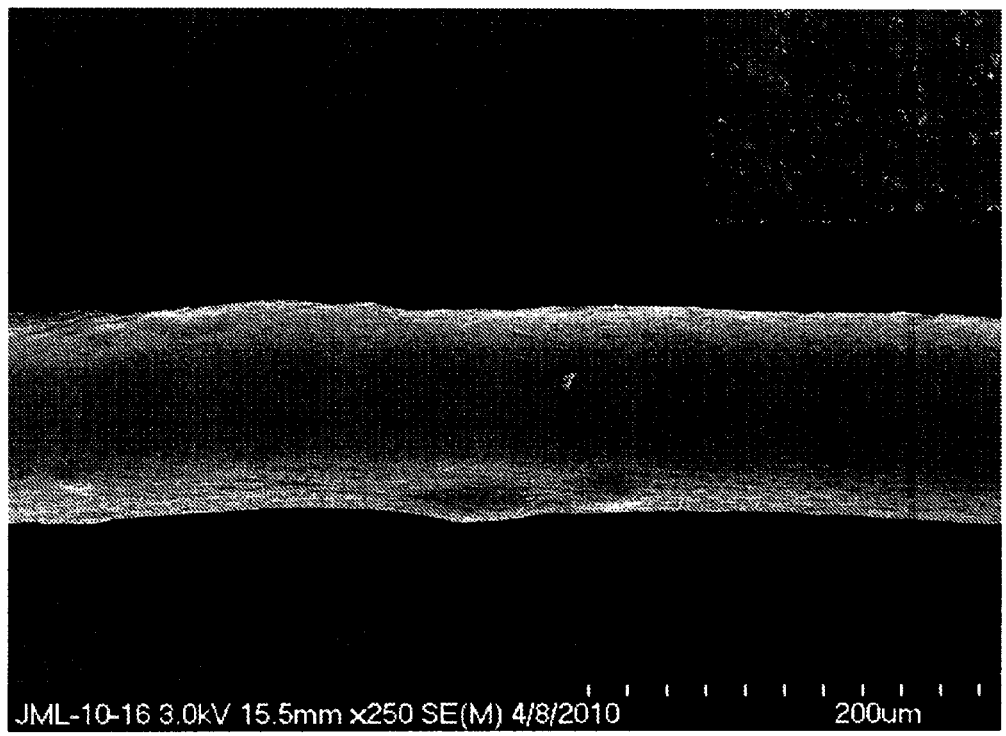
FIG. 3 is an SEM micrograph of an exemplary embodiment of a semi-permanent mascara composition coated on an artificial eyelash.
Figure 4:
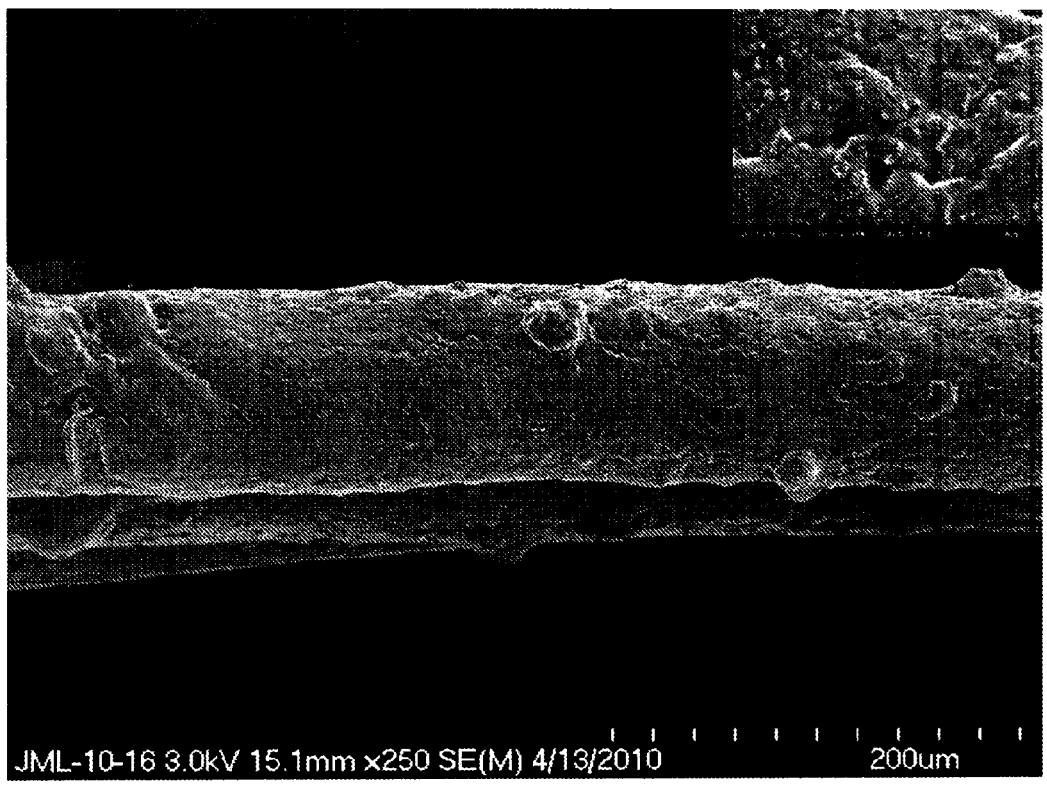
FIGS. 4-7 are SEM micrographs of conventional mascara compositions coated on an artificial eyelash.
Figure 5:
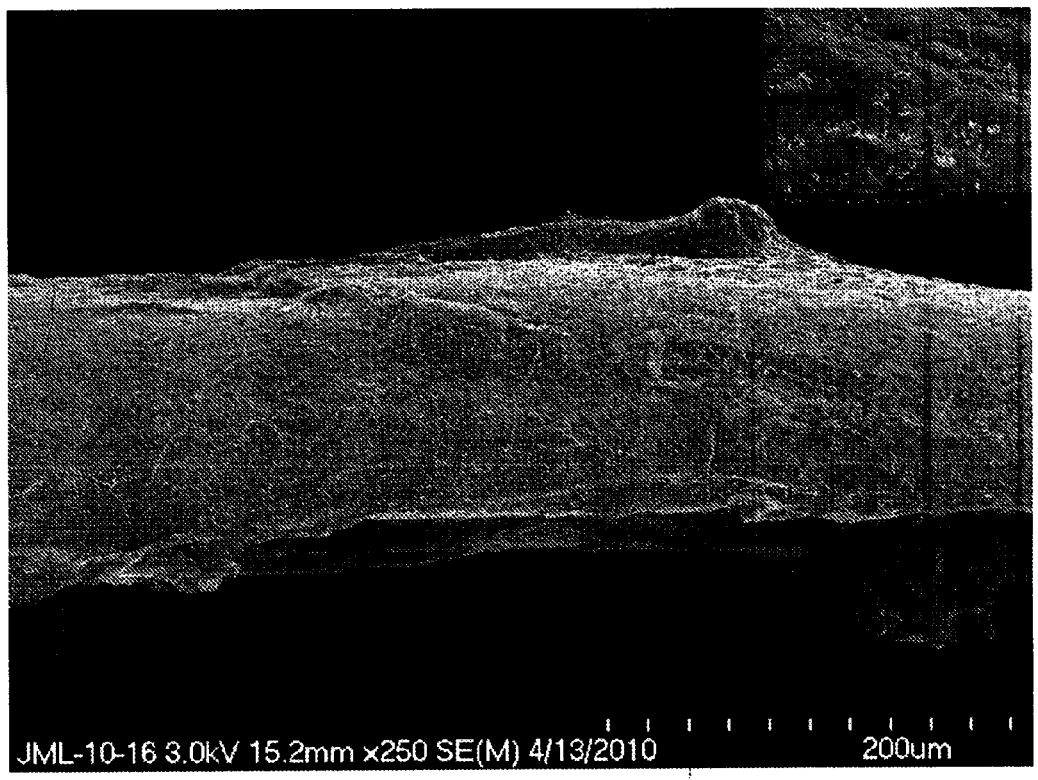
Figure 6:
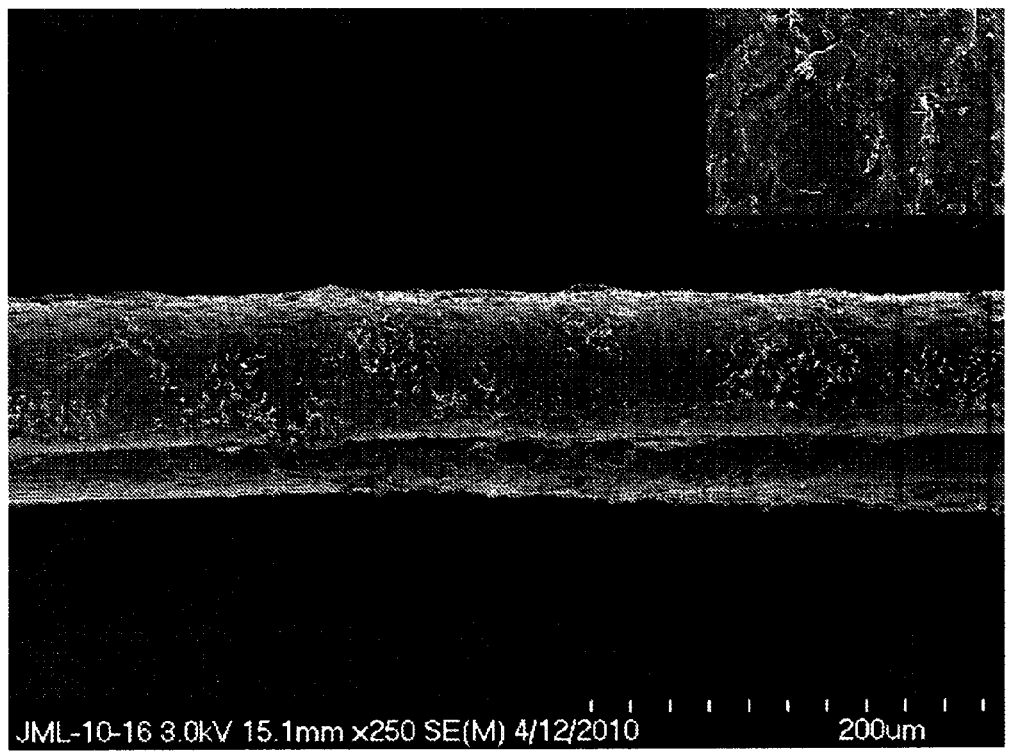
Figure 7:
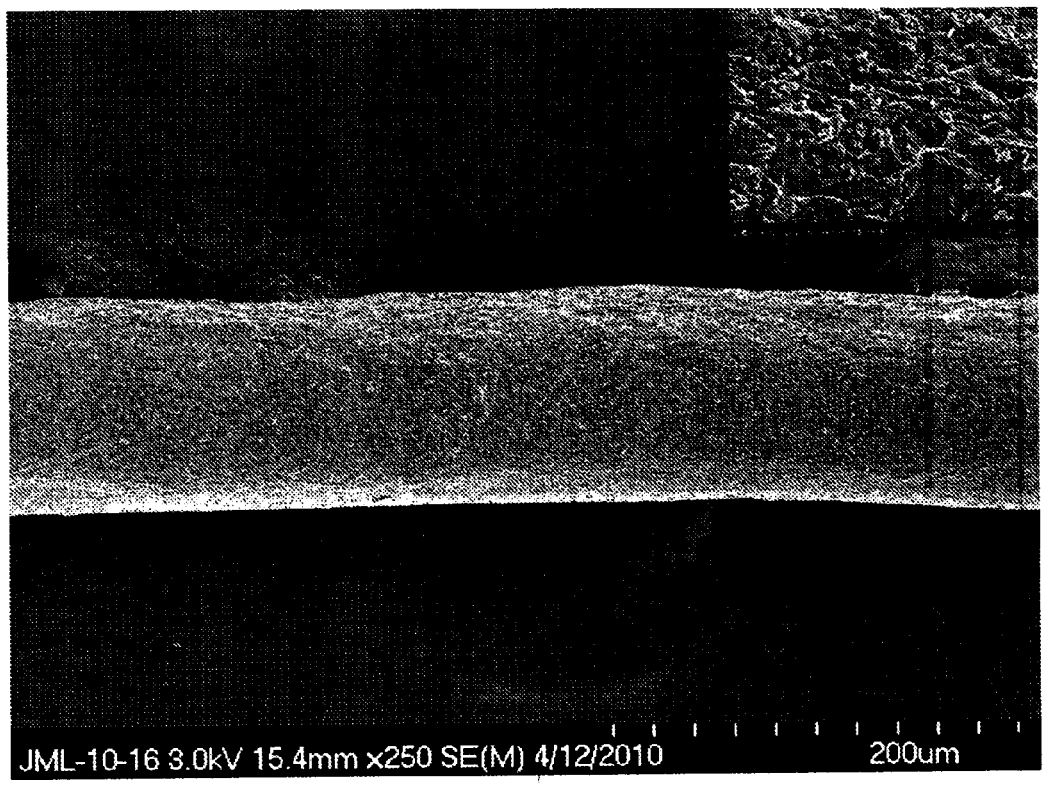

Cryo-SEM was performed on films formed from: the exemplary 017 semi-permanent mascara composition described in Table 1A, Cover Girl® Lash Exact Waterproof Very Black, Cover Girl® Lash Exact Very Black, Maybelline® XXL Pro 24HR Bold® Mascara Very Black, and Tarte® 4 day Stay Lash Stain. FIG. 3 is an SEM micrograph of a film formed from an exemplary semi-permanent mascara composition. As seen in FIG. 3, the present semi-permanent mascara provides a continuous film that smoothly coats the false eyelash. Even at increased magnification (5000×), as seen in the inset of the micrograph in FIG. 3, the surface of the film is smooth with bits of pigment (appearing as white dots) showing through. The films produced by the Tarte® 4 Day Stay Lash Stain brand mascara, Maybelline® XXL Pro 24HR Bold® brand mascara, Cover Girl® Lash Exact brand mascara, and the Cover Girl® Lash Exact Waterproof brand mascara, as illustrated in FIGS. 4-7, respectively, do not exhibit the smooth, continuous morphology of the film formed from the present semi-permanent mascara composition.

Table 2 illustrates the long-wear benefit of the present semi-permanent mascara composition compared to conventional mascaras. The Average DL values shown in Table 2 are obtained using Rub Test Method #1, described hereinabove.

TABLE 2

|  | Avg. Delta L |
| --- | --- |
| Inventive Mascara Compositions |  |
| Prototype 006 | −0.20 |
| Prototype 089 | −0.67 |
| Prototype 036 | −1.65 |
| Prototype 017 | −0.88 |
| Comparative Compositions |  |
| Cover Girl Lash Exact Water Proof Very Black ® | −2.54 |
| Cover Girl Lash Exact Very Black ® | −4.09 |
| Maybelline Define-A-Lash Waterproof Mascara Very Black ® | −5.34 |
| Tarte 4 day Stay Lash Stain ® | −7.48 |
| Maybelline XXL Pro 24 HR Bold Mascara Very Black ® | −8.49 |
| Maybelline Define-A-Lash Mascara Very Black ® | −10.70 |

As seen in Table 2, exemplary compositions 006, 036, 089 and 017 all demonstrate suitably low Average Delta L values, while the conventional mascara compositions do not. Suitable Delta L values include values of less than 2.5, 2.0, 1.5 or less, when measured according to the Rub Test.

Consumer Test #1

A study was conducted to assess the visual wear advantages of the present semi-permanent mascara composition (prototype 036 shown Table 1A and described hereinabove) versus a subset of the comparative mascaras listed in Table 1B. Prior to the application of each test product, lashes were treated the evening before with Cover Girl Clean® brand make-up remover for eyes and lips and rinsed with water to ensure that lashes were free of mascara residue when the test product was applied the following morning. Further, the test panelists were given the same facial cleanser and facial moisturizer products to use daily to ensure consistent skin treatment and consistent cleansing and skin care exposure between panelists and test products. The present semi-permanent mascara composition was applied using a Shape IV molded plastic brush available from GEKA GmbH, Bechhofen, Germany. The plastic molded brush has a core diameter of 2.28±1 mm; a brush length of 25.6±0 3 mm; a maximum brush diameter of 7.75±0.25 mm; and 228 bristles. The conventional mascaras are commercially available and were applied with the applicator included with the product. Consumer Test #1 is a multi-product test. Images were taken at baseline (bare lashes), immediately after application, 8 hours (end of day 1), 24 hours (beginning of day 2), 32 hours (end of day 2), 48 hours (beginning of day 3) and 56 hours (end of day 3). If the product continued to wear beyond the end of day 3, additional images were taken at extended time points (i.e., start of day 4 and start of day 5) until the product was judged to no longer provide the desirable appearance benefits (as determined by the test moderator). Prior to the end of day 3, if product is no longer observed, no additional images were taken. Each panelist rotated through the 5 test products randomly. Panelists were instructed to apply the product until they got to their desired end look. The images were captured on a Fujifilm FinePix S1Pro® brand camera using an external flash with a focal length of 105 mm. Consumer Test #1 demonstrated that the present semi-permanent mascara composition provides an improved mascara benefit over multiple days when compared to conventional mascaras.

Figure 8:
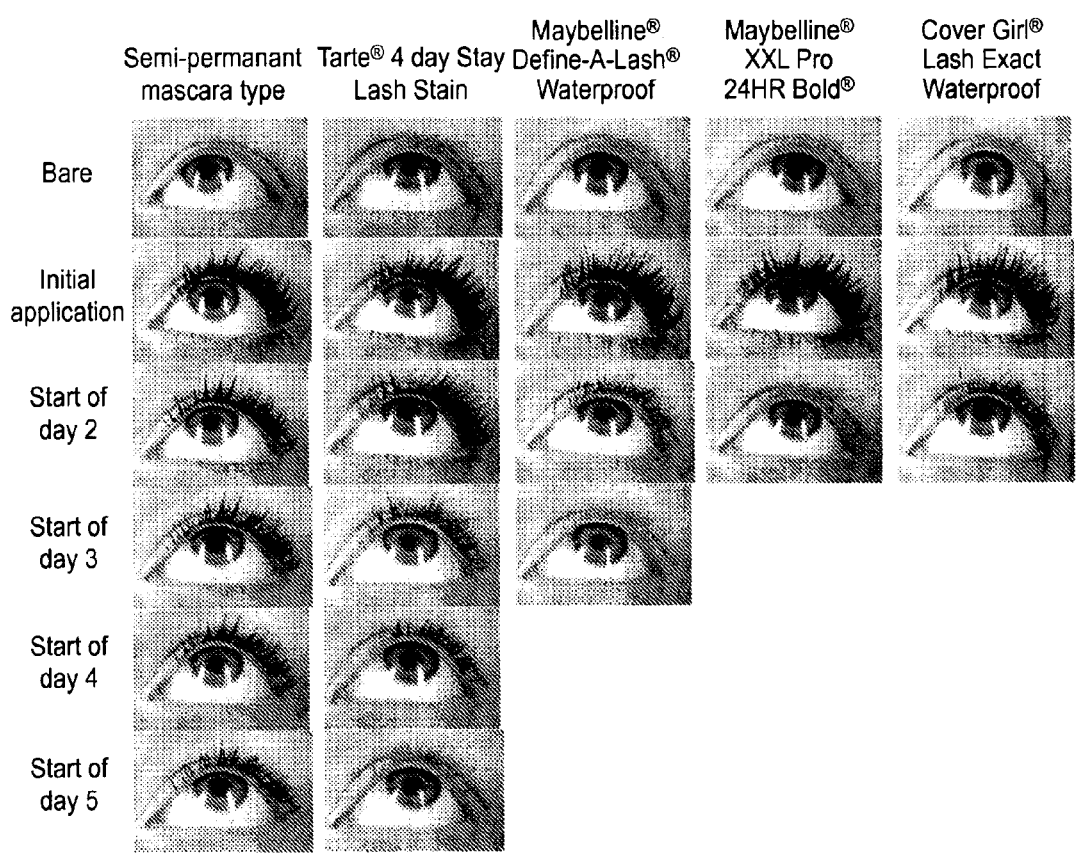
FIG. 8 illustrates the long-wear benefit of the present semi-permanent mascara composition on the eyelashes of a user.

FIG. 8 illustrates the difference in longevity of overall wear and mascara beauty benefits versus the comparative mascara set, which was demonstrated in Consumer Test #1. As can be seen in FIG. 8, all of the mascaras provide an initial beauty benefit of long, dark, full lashes relative to the bare lash image. But the comparative mascaras do not provide a suitable beauty look at the start of day 2, after normal wear, washing, and sleeping. Further, none of these products lasted beyond day 2. Although the Tarte® 4 Day Stay Lash Stain provided some darkness for multiple days, the lash length and volume conferred by the product and the longevity of product wear was not at the level of prototype 036, as shown in FIG. 8. The images in FIG. 8 clearly demonstrate that the present semi-permanent mascara composition provides superior wear and longevity of mascara beauty benefits over multiple days versus conventional mascara compositions.

Consumer Test #2

A study was conducted to assess the visual wear advantages of the present semi-permanent mascara composition, when applied with a suitable twisted-wire brush, versus applying the same product with an unsuitable molded plastic brush. The twisted-wire brush used in Consumer Test #2 is commercially available in Cover Girl® Professional Super Thick Lash brand mascara product. Each wire in the twisted-wire core of the applicator has a wire diameter of 0.70 mm; a brush head length of 25.4±1.52 mm; a minimum diameter of 4.32±0.25 mm; a maximum diameter of 7.75±0.25 mm; 600±30 hollow bristles; and 18±1 turns. The molded plastic brush used in Consumer Test #2 is a Shape IV molded plastic brush available from GEKA GmbH, Bechhofen, Germany. The plastic molded brush has a core diameter of 2.28±1 mm; a brush length of 25.6±0.3 mm; a maximum brush diameter of 7.75±0.25 mm; and 228 bristles.

Consumer Test #2 is a single-product test. Prior to the application of product, images were taken of clean, bare lashes (baseline) using a fixed rig to minimize movement during image capture. For image capture panelists were instructed to look up so that the full arc of top lashes could be seen against the brow bone. Panelists were then instructed to apply the product until they got to their desired end look. Images were taken immediately after application of the mascara, and at 24 hours (beginning of day 2). The images were captured on a Fujifilm FinePix S1Pro® brand camera using an external flash with a focal length of 105 mm. The brush type (Shape IV and Twisted Wire Brush) were tested simultaneously on each panelist (one brush type per eye). The order of application and left or right eye for each brush were randomized. The Consumer Test demonstrated that the present semi-permanent mascara composition when applied with a suitable twisted-wire brush applicator provides an improved separation and reduced clumping upon initial look (immediately after application) and over multiple days when compared to an unsuitable molded plastic brush.

Figure 11A:
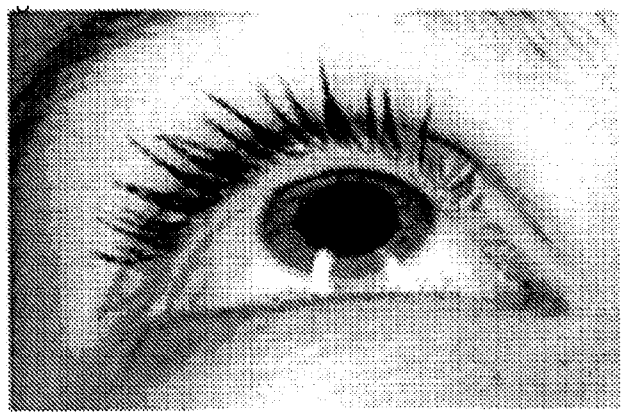
FIGS. 11A-14B illustrate the benefit of applying the present semi-permanent mascara composition with a twisted-wire brush as compared to application with a molded plastic brush.
Figure 11B:
Figure 12A:
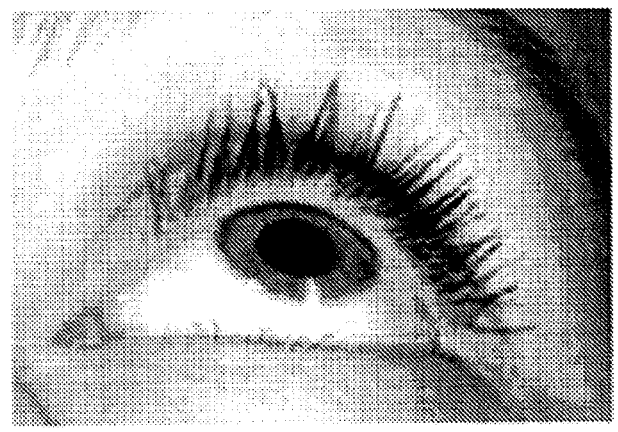
Figure 12B:
Figure 13A:
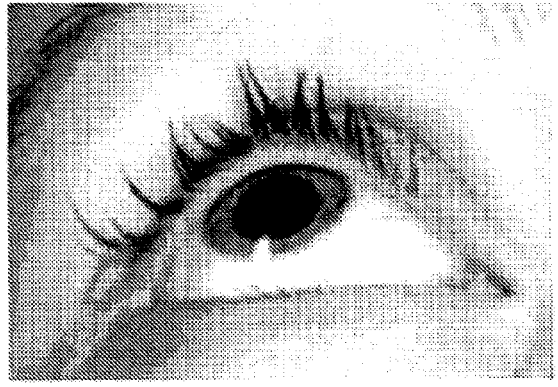
Figure 13B:
Figure 14A:
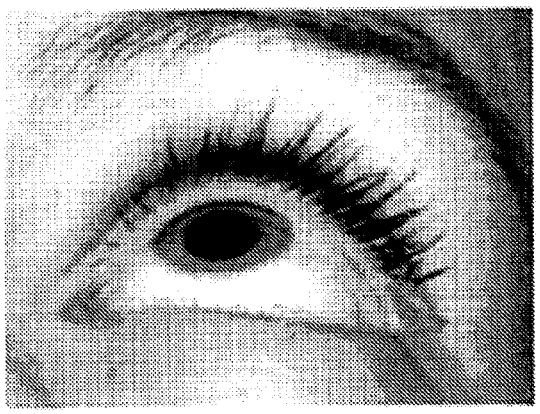
Figure 14B:

FIGS. 11A-14B illustrate the difference in the separation and clumping benefit when the present semi-permanent mascara composition is applied with a suitable applicator versus an unsuitable molded plastic applicable. FIG. 11A shows eyelashes immediately after mascara application with the molded plastic brush. FIG. 11B is a blow up view of the eyelashes in FIG. 11A. FIG. 12A shows eyelashes immediately after mascara application with the twisted-wire brush. FIG. 12B is a blow up view of the eyelashes in FIG. 12B. FIG. 13A shows eyelashes after 24 hours of mascara application with the molded plastic brush. FIG. 13B is a blow up view of the eyelashes in FIG. 13A. FIG. 14A shows eyelashes 24 hours after mascara application with the twisted-wire brush. FIG. 14B is a blow up view of the eyelashes in FIG. 14A. The images in FIGS. 11A-14B clearly demonstrate that the present semi-permanent mascara composition when applied with a suitable twisted-wire brush provides superior separation and clumping benefits initially and over multiple days versus application of the same mascara composition with a molded plastic brush.

EXAMPLE 2

The four exemplary semi-permanent mascara compositions detailed in Table 1A (i.e., 006, 017, 036, 089) were compared to three exemplary mascara compositions described in JP 2009-114099 (by Kose) to evaluate the abrasion resistance benefit of the present semi-permanent mascara compositions. Table 2A shows the comparative compositions used in the test. The method for preparing the comparative compositions is provided immediately following Table 2A.

TABLE 2A

Comparative Mascara Compositions

| No. | Component | Trade Name | Ex 1 % W | Ex 2 % W | Ex 9 % W |
|---|---|---|---|---|---|
| 1 | Hydrogenated ester gum | Pine crystal KE-311 | 8 | 15 | 8 |
| 2 | Hydrogenated Pentaerythrityl Rosinate | Ester gum HP | 8 | 10 | 8 |
| 3 | Carnauba Wax | | 3 | 3 | 3 |
| 4 | Beeswax | | 5 | 5 | 5 |
| 5 | Dextrin fatty acid ester | Rheopearl TL | 3 | 3 | — |
| 6 | Organic modified bentonite | | 2 | 2 | 2 |
| 7 | Silicone-treated black iron oxide | 5% dimethicone treatment | 8 | 8 | 8 |
| 8 | Talc | | 5 | 5 | 5 |
| 9 | Sericite | | 2 | 2 | 2 |
| 10 | Silicic anhydride | Aerosil 200 | 2 | 2 | 2 |
| 11 | Light liquid isoparaffin | IP Sorbent 1620MU | qs | qs | qs |
| | TOTAL | | 100 | 100 | 100 |

Examples 1, 2, and 9 of JP 2009-114099 were prepared as follows:

A. Components 1-3 were heated to about 110° C. and mixed to homogeneity.

B. Components 4-11 were added to A and mixed to homogeneity.

C. The composition of step B was placed in containers to obtain oil-based mascaras.

The Rub Test was used to evaluate the abrasion resistance of each of the compositions. As shown in Table 2B, the present semi-permanent mascara compositions exhibit a suitable Average Delta L, while the comparative compositions do not.

TABLE 2B

Rub Test Results

| | Avg. Delta L |
|---|---|
| Inventive Mascara Compositions | |
| Prototype 006 | −0.20 |
| Prototype 017 | −0.88 |
| Prototype 036 | −1.65 |
| Prototype 089 | −0.67 |
| Comparative Compositions | |
| JP 2009-114099 Mascara Example # 1 | −3.56 |
| JP 2009-114099 Mascara Example # 2 | −4.70 |
| JP 2009-114099 Mascara Example # 9 | −4.27 |

EXAMPLE 3

Table 3 lists the composition for an exemplary top coat for use over the present mascara compositions.

TABLE 3

Top Coat Composition

| Raw Material Description | Supplier/Trade Name | Function | % Wt/Wt |
|---|---|---|---|
| Isododecane | Presperse Permthyl 99A | Volatile Solvent | 49.995% |
| Trimethylsiloxysilicate | Momentive MQ Resin | Film Former | 38.025% |
| Dimethicone | Momentive SE-30 Gum | Film Former | 10.980% |
| 1,2 Hexanediol, Caprylyl Glycol | Symrise Symdiol 68 | Preservative | 1.000% |
| | | TOTAL | 100.000% |

EXAMPLE 4

Another exemplary semi-permanent mascara composition.

TABLE 4

Semi-Permanent Mascara Composition

| Phase | Material | Wt % |
|---|---|---|
| A | Isododecane | 45.5 |
| A | 1,2 Hexanediol and Caprylyl Glycol | 1 |
| A | Benzyl Alcohol | 0.65 |
| B | Tall Oil Glycerides | 13.5 |
| B | Pentaerythrityl Hydrogenated Rosinate | 13.5 |
| C | Black Iron Oxide (Jet Milled) | 10 |
| D | Disteardimonium Hectorite | QS |

Phase A ingredients are melted and mixed together with low shear mixing. Phase B is gradually added to the Phase A and then dispersed with high shear mixing. Phase C is then added and dispersed with high shear mixing. Phase D is added and the batch is cooled to ambient conditions.

EXAMPLE 5

Several conventional multi-day/long-wear mascaras and a lash stain were tested to compare the clumping effect of conventional mascara products to the present long-wear mascara. Table 5 shows the name and code of the mascara tested and illustrates the average W.A.T. value at 1 stroke, 3 strokes and 5 strokes. The brush used to apply each of the comparative mascaras is the brush that is sold with the commercially available product. A general description of the brush is provided in Table 5. Prototype 036, which is described above, was applied with a molded plastic brush and a twisted wire brush to demonstrate the reduced clumping benefit. The molded plastic brush is a Shape 4 molded plastic brush available from GEKA, GmbH. The twisted wire brush is a 2000 Calorie brand twisted wire brush available from Alcan Packaging Beauty Services, France. The mascaras tested were Clinique® Lash Power® brand mascara, Clinique® High Impact Curling™ brand mascara, Tarte® 4 day brand lash stain, Max Factor® False Lash Effect 24® brand mascara, Maybelline® Define-a-Lash® brand waterproof mascara, Maybelline® Volume' Express® Falsies® brand waterproof mascara, Lorac® 3 day brand mascara, Santoprene® brand mascara, Hard Candy® brand mascara and L'Oreal Beauty Tubes™. The clumping level was determined according to the W.A.T. Test described above.

TABLE 5

| Product | Brush type | Code | | Average W.A.T. |
|---|---|---|---|---|
| Clinique Lash Power | twisted wire | CLP | 1 Stroke | 51.6 |
| | | | 3 stroke | 52.2 |
| | | | 5 Stroke | 56.8 |
| Clinique High Impact Curl | twisted wire | CHI | 1 Stroke | 39.8 |
| | | | 3 stroke | 43.1 |
| | | | 5 Stroke | 45.0 |
| Tarte 4 day | twisted wire | TA | 1 Stroke | 20.8 |
| | | | 3 stroke | 31.1 |
| | | | 5 Stroke | 31.3 |
| prototype 036 | twisted wire | GTWB | 1 Stroke | 30.7 |
| | | | 3 stroke | 22.9 |
| | | | 5 Stroke | 24.7 |
| prototype 036 | rubber | GS | 1 Stroke | 67.1 |
| | | | 3 stroke | 69.7 |
| | | | 5 Stroke | 69.3 |
| False Lash Effect 24 | rubber | FLE 24 | 1 Stroke | 33.1 |
| | | | 3 stroke | 35.8 |
| | | | 5 Stroke | 38.0 |
| Maybelline Define A Lash Water proof | rubber | MDAL | 1 Stroke | 22.7 |
| | | | 3 stroke | 25.2 |
| | | | 5 Stroke | 36.4 |
| Maybelline Define A Lash | Rubber | MDAL R | 1 Stroke | 25.5 |
| | | | 3 stroke | 28.1 |
| | | | 5 Stroke | 27.8 |
| Maybelline Falsies Water proof | twisted wire | MFWP | 1 Stroke | 32.9 |
| | | | 3 stroke | 46.7 |
| | | | 5 Stroke | 55.1 |
| Lorac 3 day | twisted wire | L3D | 1 Stroke | 19.2 |
| | | | 3 stroke | 26.8 |
| | | | 5 Stroke | 31.5 |
| Hard Candy | twisted wire | HC | 1 Stroke | 20.7 |
| | | | 3 stroke | 28.6 |
| | | | 5 Stroke | 36.0 |
| Beauty tubes (2 Step) | twisted wire | BT | 1 Stroke | 39.1 |
| | | | 3 stroke | 41.7 |
| | | | 5 Stroke | 46.0 |
| Beauty tubes top coat only | twisted wire | BT1 | 1 Stroke | 33.1 |
| | | | 3 stroke | 34.9 |
| | | | 5 Stroke | 41.5 |

As seen in Table 5, the present long-wear mascara in combination with the twisted wire brush provides superior anti clumping benefit at the beauty end state (i.e., fifth stroke). In addition, as illustrated in FIG. 18, the present long-wear mascara composition in combination with the twisted wire brush is the only sample tested to exhibit a positive value when going from the first stroke to the third stroke (sometimes referred to as a "dump and fix" profile). That is, the first stroke W.A.T. value is greater than the third stroke W.A.T. value, which indicates a reduction in clumping from the first stroke to the third stroke. Suitable dump and fix profiles may have a change in W.A.T. value from the first to the third stroke of at least 1, 2, 3, 4, 5, 6, 7, 8, 9, 10 or more). Additionally or alternatively, it may be desirable to configure the present mascara product such that the W.A.T. values measured at 3 strokes and 5 strokes are both greater than the W.A.T. value at the first stroke.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mascara product comprising:
   a. a container for storing and dispensing mascara;
   b. a liquid mascara composition disposed in the container, the liquid mascara composition comprising
      i. from about 1-60% by weight of black iron oxide particles as a colorant
      ii. from 10-80% by weight of isododecane as the volatile carrier
      iii. from 15-35% of mixture of tall oil glycerides and pentaerythrityl hydrogenated rosinate as film-formers
      iv. from 1-25% of a disteardimonium hectorite having a diameter less than 10 microns as a thickener wherein said liquid mascara composition has a volume concentration of solids that is below the critical pigment volume concentration, and the viscosity of said liquid mascara composition is in the range of 250,000-350,000 cps as measured by Brookfield brand RTV viscometer using a TE spindle at 10 rpm and 25° C., and said liquid mascara composition is free of wax
   c. a twisted-wire brush applicator that includes a between 400 and 800 fiber bristles securely joined to a twisted-wire core, the twisted-wire brush applicator including a handle and a stem joining the handle to the twisted-wire core, the handle being removably and reattachably joined to the container;
   d. liquid wherein the mascara composition has a Delta L value of less than 2.5 according to the Rub Test and the mascara product has a Weighted Average Thickness value at five strokes of less than 30 according to the Weighted Average Thickness test.

* * * * *